United States Patent
Sakurai et al.

(10) Patent No.: US 12,146,146 B2
(45) Date of Patent: Nov. 19, 2024

(54) METHOD FOR PRODUCING TRANS-POLYISOPRENOID, VECTOR, TRANSGENIC PLANT, METHOD FOR PRODUCING PNEUMATIC TIRE AND METHOD FOR PRODUCING RUBBER PRODUCT

(71) Applicants: SUMITOMO RUBBER INDUSTRIES, LTD., Kobe (JP); TOHOKU UNIVERSITY, Sendai (JP); KANAZAWA UNIVERSITY, Kanazawa (JP)

(72) Inventors: Yuko Sakurai, Kobe (JP); Haruhiko Yamaguchi, Kobe (JP); Yukino Inoue, Kobe (JP); Kazuhisa Fushihara, Kobe (JP); Seiji Takahashi, Sendai (JP); Satoshi Yamashita, Kanazawa (JP); Toru Nakayama, Sendai (JP)

(73) Assignees: SUMITOMO RUBBER INDUSTRIES, LTD., Kobe (JP); TOHOKU UNIVERSITY, Sendai (JP); KANAZAWA UNIVERSITY, Kanazawa (JP)

( * ) Notice: Subject to any disclaimer, the term of this patent is extended or adjusted under 35 U.S.C. 154(b) by 92 days.

(21) Appl. No.: 17/412,891

(22) Filed: Aug. 26, 2021

(65) Prior Publication Data
US 2022/0002759 A1    Jan. 6, 2022

Related U.S. Application Data

(62) Division of application No. 16/466,193, filed as application No. PCT/JP2017/041732 on Nov. 21, 2017, now abandoned.

(30) Foreign Application Priority Data

Dec. 21, 2016 (JP) ................................. 2016-248330

(51) Int. Cl.
C12N 15/82    (2006.01)
A01H 6/00    (2018.01)
B60C 1/00    (2006.01)
C12P 5/02    (2006.01)

(52) U.S. Cl.
CPC ............ C12N 15/8243 (2013.01); *A01H 6/00* (2018.05); *B60C 1/00* (2013.01); *C12P 5/02* (2013.01)

(58) Field of Classification Search
CPC .......................... C12N 15/8243; C12P 5/007
See application file for complete search history.

(56) References Cited

U.S. PATENT DOCUMENTS

| | | | |
|---|---|---|---|
| 9,127,286 B2 * | 9/2015 | Nakazawa | C12N 9/1085 |
| 10,000,774 B2 | 6/2018 | Yamaguchi | |
| 10,385,362 B2 | 8/2019 | Inoue et al. | |
| 11,236,365 B2 | 2/2022 | Inoue et al. | |
| 2003/0236208 A1 | 12/2003 | Kmiec et al. | |
| 2007/0199099 A1 | 8/2007 | Hallahan et al. | |
| 2009/0288226 A1 | 11/2009 | Hallahan et al. | |
| 2010/0218272 A1 | 8/2010 | Nakazawa et al. | |
| 2011/0201771 A1 * | 8/2011 | Puskas | C08F 136/08 |
| | | | 435/167 |
| 2015/0266988 A1 | 9/2015 | Kojima et al. | |
| 2015/0322446 A1 | 11/2015 | Yamaguchi et al. | |
| 2016/0244773 A1 | 8/2016 | Inoue et al. | |
| 2016/0244775 A1 | 8/2016 | Inoue et al. | |
| 2016/0244776 A1 | 8/2016 | Inoue et al. | |
| 2017/0051313 A1 | 2/2017 | Inoue et al. | |
| 2018/0171364 A1 | 6/2018 | Yamaguchi et al. | |
| 2019/0323039 A1 | 10/2019 | Inoue et al. | |
| 2019/0376093 A1 | 12/2019 | Sakurai et al. | |

FOREIGN PATENT DOCUMENTS

| | | |
|---|---|---|
| CN | 104684987 A | 6/2015 |
| EP | 3 097 775 A1 | 11/2016 |
| EP | 3 309 257 A1 | 4/2018 |
| JP | 2003-18999 A | 1/2003 |
| JP | 2003-310295 A | 11/2003 |
| JP | 2005-500840 A | 1/2005 |
| JP | 2005-225796 A | 8/2005 |

(Continued)

OTHER PUBLICATIONS

Friedberg (Automated protein function prediction—the genomic challenge. Brief. Bioinformatics. 7:225-242, 2006) (Year: 2006).*
Wang et al (From Protein Sequence to Protein Function via Multi-Label Linear Discriminant Analysis. IEEE/ACM Transactions on Computational Biology and Bioinformatics, vol. 14, No. 3, 503-513, 2017) (Year: 2017).*
Yamashita et al (Identification and reconstitution of the rubber biosynthetic machinery on rubber particles from Hevea brasiliensis. eLIFE, 1-28, Oct. 2016) (Year: 2016).*

(Continued)

*Primary Examiner* — Charles Logsdon
*Assistant Examiner* — Wayne Zhong
(74) *Attorney, Agent, or Firm* — Birch, Stewart, Kolasch & Birch, LLP

(57) ABSTRACT

The present invention aims to provide a method for producing a trans-polyisoprenoid which can increase trans rubber production. The present invention is directed to a method for producing a trans-polyisoprenoid in vitro, which involves the use of a gene coding for a trans-prenyltransferase (tPT) family protein and further involves the use of rubber particles bound to a protein encoded by the gene, or a method for producing a trans-polyisoprenoid, which includes introducing into a plant a vector including a promotor having a promoter activity that drives laticifer-specific gene expression and a gene coding for a tPT family protein linked to the promotor to express a protein encoded by the gene specifically in laticifers.

7 Claims, 3 Drawing Sheets

Specification includes a Sequence Listing.

(56) References Cited

FOREIGN PATENT DOCUMENTS

| | | |
|---|---|---|
| JP | 2005-308412 A | 11/2005 |
| JP | 2005-312436 A | 11/2005 |
| JP | 2009-221306 A | 10/2009 |
| JP | 2010-119373 A | 6/2010 |
| JP | 2010-132594 A | 6/2010 |
| JP | 2011-52146 A | 3/2011 |
| JP | 2011-188776 A | 9/2011 |
| JP | 5035871 B2 | 9/2012 |
| JP | 2014-11972 A | 1/2014 |
| JP | 5383197 B2 | 1/2014 |
| JP | 2014-227487 A | 12/2014 |
| JP | 2015-136296 A | 7/2015 |
| JP | 2016-93186 A | 5/2016 |
| JP | 2016-149973 A | 8/2016 |
| JP | 2016-154458 A | 9/2016 |
| WO | WO 03/010294 A2 | 2/2003 |
| WO | WO 2004/044173 A2 | 5/2004 |
| WO | WO 2004/106531 A1 | 12/2004 |
| WO | WO 2018/116726 A1 | 6/2018 |

OTHER PUBLICATIONS

Nozawa et al (Chapter 17. Production of membrane proteins through the wheat-germ cell-free technology. Springer Protocol, 213-218, 2010). (Year: 2010).*

Murota et al (*Arabidopsis* Cell-Free Extract, ACE, a New In Vitro Translation System Derived from *Arabidopsis callus* Cultures. Plant Cell Physiol. 52: 1443-1453, 2011) (Year: 2011).*

Phatthiya et al (Cloning and expression of the gene encoding solanesyl diphosphate synthase from Hevea brasiliensis. Plant Science 172. 824-831, 2007) (Year: 2007).*

Harbers (Wheat germ systems for cell-free protein expression. FEBS Letters 588: 2762-2773, 2014). (Year: 2014).*

Bennett, "Sunflowers Make Rubber a Reality," https://www.agweb.com/news/crops/sunflowers-make-rubber-reality (2017), pp. 1-4.

Aoki et al., "Identification of Laticifer-specific Genes and their Promoter Regions from a Natural Rubber Producing Plant *Hevea brasiliensis*," Plant Science, vol. 225, 2014 (Available online May 12, 2014), pp. 1-8.

Asawatreratanakul et al., "Molecular Cloning, Expression and Characterization of cDNA Encoding cis-prenyltransferases from Hevea brasiliensis," Eur. J. Biochem., vol. 270, 2003, pp. 4671-4680.

Berthelot et al., "Hevea brasiliensis REF (Hev b 1) and SRPP (Hev b 3): An Overview on Rubber Particle Proteins," Biochimie, vol. 106, 2014 (Available online Jul. 11, 2014), pp. 1-9.

Branden et al., "Introduction to Protein Structure," Garland Publishing Inc., New York, 1991, p. 247 (3 pages total).

Brasher et al., "A Two-component Enzyme Complex is Required for Dolichol Biosynthesis in Tomato," The Plant Journal, vol. 82, 2015 (published online Apr. 21, 2015), pp. 903-914.

Dai et al., "In-depth proteome analysis of the rubber particle of *Hevea brasiliensis* (para rubber tree)," Plant Molecular Biology, vol. 82, 2013 (published online Apr. 4, 2013), pp. 155-168.

Epping et al., "A rubber transferase activator is necessary for natural rubber biosynthesis in dandelion," Nature Plants, vol. 1, Article No. 15048, May 2015 (published Apr. 27, 2015), XP055372960, pp. 1-9.

Goodman, "Polymer biosynthesis: Rubber ramps up," Nature Chemical Biology, vol. 11, No. 7, Jul. 2015, p. 448, XP055373184.

Harrison et al., "Nogo-B receptor is necessary for cellular dolichol biosynthesis and protein N-glycosylation," The EMBO Journal, vol. 30, No. 12, 2011 (published online May 13, 2011), pp. 2490-2500.

Hillebrand et al., "Down-Regulation of Small Rubber Particle Protein Expression Affects Integrity of Rubber Particles and Rubber Content in Taraxacum brevicorniculatum," PLoS ONE, vol. 7, Issue 7, e41874, Jul. 23, 2012, pp. 1-9.

Hoffman et al., "The Who, What, and Where of Plant Polyprenol Biosynthesis Point to Thylakoid Membranes and Photosynthetic Performance," The Plant Cell, vol. 29, Jul. 2017, pp. 1552-1553.

International Preliminary Report on Patentability and Written Opinion of the International Searching Authority for International Application No. PCT/JP2017/041732, dated Jun. 25, 2019.

International Search Report for International Application No. PCT/JP2016/065942, dated Jun. 28, 2016.

International Search Report for International Application No. PCT/JP2016/069172, dated Sep. 6, 2016, with English translation.

International Search Report for International Application No. PCT/JP2017/041732, dated Feb. 20, 2018.

Laibach et al., "Identification of a Taraxacum Brevicorniculatum Rubber Elongation Factor Protein that is Localized on Rubber Particles and Promotes Rubber Biosynthesis," The Plant Journal, vol. 82, 2015 (published online Mar. 24, 2015), pp. 609-620.

Madin et al., "A Highly Efficient and Robust Cell-free Protein Synthesis System Prepared from Wheat Embryos: Plants Apparently Contain a Suicide System Directed at Ribosomes," Proceedings of the National Academy of Sciences USA, vol. 97, No. 2, Jan. 18, 2000, pp. 559-564 (7 pages total).

Montoro et al., Biotechnologies in rubber tree (*Hevea brasiliensis*), Asian Pacific Conference on Tissue Culture and Agribiotechnology, Malaysia, Jun. 17-21, 2007, pp. 1-3.

Nguyen et al., "cis-Prenyltransferase Interacts with a Nogo-B Receptor Homolog for Dolichol Biosynthesis in Panax ginseng Meyer," Journal of Ginseng Research, vol. 41, 2017 (Available online Jan. 27, 2017), pp. 403-410.

Ohya et al., "Biosynthesis of Natural Rubber and Other Natural Polyisoprenoids," Biopolymers Online, Published online Jan. 15, 2005, 43 pages.

Park et al., "Mutation of Nogo-B receptor, a subunit of cis-prenyitransferase, causes a congenital disorder of glycosylation," Cell Metabolism, vol. 20, Sep. 2, 2014 (published Jul. 24, 2014), pp. 448-457.

Phatthiya et al., "Cloning and Expression of the Gene Encoding Solanesyl Diphosphate Synthase from Hevea Brasiliensis", Plant Science, vol. 172, 2007, pp. 824-831.

Post et al., "Laticifer-Specific cis-Prenyltransferase Silencing Affects the Rubber, Triterpene, and Inulin Content of Taraxacum brevicorniculatum," Plant Physiology, Mar. 2012, vol. 158, pp. 1406-1417.

Priya et al., "Differential expression pattern of rubber elongation factor (REF) mRNA transcripts from high and low yielding clones of rubber tree (*Hevea brasiliensis* Muell. Arg.)," Plant Cell Reports, vol. 26, 2007 (Published online Jul. 14, 2007), pp. 1833-1838.

Priya et al., "Molecular Cloning and Characterization of the Rubber Elongation Factor Gene and its Promoter Sequence from Rubber Tree (*Hevea brasiliensis*): A Gene Involved in Rubber Biosynthesis," Plant Science, vol. 171, 2006 (published online Jun. 13, 2006), pp. 470-480.

Qu et al., "A lettuce (*Lactuca sativa*) homolog of human Nogo-B receptor interacts with cis-prenyltransferase and is necessary for natural rubber biosynthesis," J. Biol. Chem., vol. 290, No. 4, Jan. 23, 2015, 2 pages, abstract provided only.

Rahman et al., "Draft genome sequence of the rubber tree *Hevea brasiliensis*," BMC Genomics, vol. 14, No. 75, 2013, pp. 1-15.

Rahman et al., "TSA: Hevea brasiliensis contig33814, mRNA sequence," Database Gen Bank [online], Accession No. JT945746, Feb. 5, 2013, pp. 1-2.

Results from BLAST® search for sequences producing significant alignments relative to SEQ ID No. 1 in the GenBank, obtained on Jun. 28, 2021.

Results from BLAST® search for sequences producing significant alignments relative to SEQ ID No. 3 in the GenBank, obtained on Jun. 28, 2021.

Results from BLAST® search for sequences producing significant alignments relative to SEQ ID No. 5 in the GenBank, obtained on Jun. 28, 2021.

Rojruthai et al., "In Vitro Synthesis of High Molecular Weight Rubber by Hevea Small Rubber Particles," Journal of Bioscience and Bioengineering, vol. 109, No. 2, 2010 (Available online Sep. 18, 2009), pp. 107-114.

Sunderasan et al., "Incidence of Self- and Cross-pollination in Two Hevea brasilieness Clones," J. Nat. Rubb. Res. (1994), vol. 9, No. 4, pp. 253-257.

(56) References Cited

OTHER PUBLICATIONS

Surmacz et al., "cis-Prenyltransferase AtCPT6 produces a family of very short-chain polyisoprenoids in planta," Biochimica et Biophysica Acta, vol. 1841, 2014 (available online Dec. 1, 2013), pp. 240-250.

Takahashi et al., "Characterization of cis-prenyltransferases from the rubber producing plant *Hevea brasiliensis* heterologously expressed in yeast and plant cells," Plant Biotechnology, vol. 29, Oct. 20, 2012 (published online Aug. 30, 2012), pp. 411-417 (8 pages total).

Takahashi et al., "Molecular Insights of Natural Rubber Biosynthesis—An Approach from Prenyltransferase Gene Analysis", The Society of Rubber Science and Technology, vol. 76, No. 12, 2003, pp. 446-452, with 1 page abstract.

Tata et al., "Lacticifer Tissue-Specific Activation of the Hevea SRPP Promoter in Taraxacum brevicorniculatum and its Regulation by Light, Tapping and Cold Stress," Industrial Crops and Products, vol. 40, 2012, pp. 219-224.

Unknown, "Successful in Vitro Synthesis of Natural Rubber by Bioengineering—Contributing to the Stable Supply of Natural Rubber with New Molecular Structure", Tohoku University, Nov. 16, 2016, 4 pages total.

Xiang et al., "Proteome Analysis of the Large and the Small Rubber Particles of Hevea brasiliensis Using 2D-DIGE," Plant Physiology and Biochemistry, vol. 60, 2012 (Available online Sep. 5, 2012), pp. 207-213.

Yamashita et al., "Identification and Reconstitution of the Rubber Biosynthetic Machinery on Rubber Particles from Hevea Brasiliensis", eLife, vol. 5, No. 19022, Oct. 28, 2016, pp. 1-28.

Yokoyama, "Development of Membrane Protein-synthesizing System Without Using Cells", NPG Nature Asia-Pacific, vol. 7, No. 4-5, 2010, pp. 28-29, with English translation.

Tian et al., "Hevea brasiliensis MYC1 (MYC1) gene, promoter region and 5' UTR," Chinese Academy of Tropical Agricultural Sciences, HM590649, Jun. 30, 2012, 3 pages total.

Zhao et al., "MYC genes with differential responses to tapping, mechanical wounding, ethrel and methyl jasmonate in laticifers of rubber tree (*Hevea brasiliensis* Muell. Arg.)," Journal of Plant Physiology, vol. 168, 2011, pp. 1649-1658.

\* cited by examiner

METHOD FOR PRODUCING TRANS-POLYISOPRENOID, VECTOR, TRANSGENIC PLANT, METHOD FOR PRODUCING PNEUMATIC TIRE AND METHOD FOR PRODUCING RUBBER PRODUCT

CROSS REFERENCE TO RELATED APPLICATIONS

This application is a Divisional of copending application Ser. No. 16/466,193, filed on Jun. 3, 2019, which is the National Phase under 35 U.S.C. § 371 of International Application No. PCT/JP2017/041732, filed on Nov. 21, 2017, which claims the benefit under 35 U.S.C. § 119(a) to Patent Application No. 2016-248330, filed in Japan on Dec. 21, 2016, all of which are hereby expressly incorporated by reference into the present application.

SEQUENCE LISTING

The instant application contains a Sequence Listing which was previously submitted in ASCII format via EFS-Web on Jun. 3, 2019, and transferred to the present application upon filing, and is hereby incorporated by reference in its entirety. Said ASCII copy, created on Jun. 3, 2019, is named 2019-06-03-SequenceListing-5051-0524PUS1.txt, and is 40 KB in size.

TECHNICAL FIELD

The present invention relates to a method for producing a trans-polyisoprenoid, a vector, a transgenic plant, a method for producing a pneumatic tire, and a method for producing a rubber product.

BACKGROUND ART

At present, natural rubber (one example of polyisoprenoids) for use in industrial rubber products is produced by cultivating rubber-producing plants, such as para rubber tree (*Hevea brasiliensis*) of the family Euphorbiaceae or Indian rubber tree (*Ficus elastica*) of the family Moraceae. Such natural rubber is a polyisoprenoid (cis-natural rubber) in which isoprene units are linked in a cis configuration. Other polyisoprenoids in which isoprene units are trans-linked, trans-polyisoprenoids (trans rubber), also exist in the nature.

A few plants in the nature, such as *Eucommia ulmoides* belonging to the family Eucommiaceae of the order Eucommiales, a high deciduous tree native to China, are known to produce trans-polyisoprenoids (trans rubber) which can be extracted from the seeds or pericarp tissue of *Eucommia ulmoides*. Trans rubber can also be chemically synthesized. Such trans rubber has different characteristics from cis-natural rubber and has been used in crack-resistant golf balls or dental materials used to fill cavities in teeth.

The trans-polyisoprenoid extracted and purified from *Eucommia ulmoides* is a polyisoprenoid having a weight average molecular weight of about $1.8 \times 10^6$ in which at least 99% of the units of the straight chain are trans-linked, and has been used as *eucommia* lastomer. However, if *Eucommia ulmoides*, which is used as a healthy food or herbal medicine, is industrially used to extract and purify a trans-polyisoprenoid, this may potentially compete with use as a food material.

Meanwhile, the chemically synthesized trans-polyisoprenoids do not have a trans content of 100% but contain about 1.2 to 4% of cis bonds. They also have a molecular weight of about 250,000, and it is very difficult to synthesize a trans-polyisoprenoid having an ultra-high molecular weight of 1,000,000 or higher. Furthermore, their chemical synthesis requires a supply of raw materials, including petroleum-derived materials, which is hardly an eco-friendly (environmentally friendly) procurement process.

As described, both methods based on extraction and purification from *Eucommia ulmoides* and on chemical synthesis may cause a problem associated with energy or competition with foodstuff. There is therefore a need for methods capable of stable and large quantity procurement of trans-polyisoprenoids (trans rubber).

Trans rubber has a trans-1,4-polyisoprene structure that is biosynthesized by addition polymerization of isopentenyl diphosphate (IPP) with a starting substrate such as dimethylallyl diphosphate (DMAPP) or farnesyl diphosphate (FPP), and the nature of this structure suggests that a trans-prenyltransferase (tPT) may be involved in trans rubber biosynthesis.

For example, Patent Literature 1 describes that trans-1,4-polyisoprene can be efficiently produced by transforming a plant with an expression vector containing a gene coding for a long-chain trans-prenyl diphosphate synthase (trans-prenyltransferase) to produce a plant containing an increased amount of trans-1,4-polyisoprene, and cultivating the plant.

CITATION LIST

Patent Literature

Patent Literature 1: JP 2016-93186 A

SUMMARY OF INVENTION

Technical Problem

As discussed above, a need has existed for methods capable of stable and large quantity procurement of trans-polyisoprenoids (trans rubber). Unfortunately, very little research and development has been devoted to such methods, and there is still much room for improvement in terms of methods for stable and large quantity procurement of trans-polyisoprenoids (trans rubber).

In this context, one possible approach to solving these problems is to stabilize and enhance the activity of tPT in trans rubber biosynthesis in order to increase trans rubber production.

The present invention aims to solve the problems and provide a method for producing a trans-polyisoprenoid which can increase trans rubber production in vitro.

The present invention also aims to solve the above problems and provide a vector that can be introduced into a plant using genetic transformation techniques to enhance trans-polyisoprenoid production. Further objects are to provide a transgenic plant into which the vector has been introduced and to provide a method for enhancing production of a trans-isoprenoid or trans-polyisoprenoid in a plant by introducing the vector into the plant.

Solution to Problem

The present invention relates to a method for producing a trans-polyisoprenoid, the method including binding a protein expressed from a gene coding for a trans-prenyltransferase (tPT) family protein to rubber particles in vitro. This invention is hereinafter called the first aspect of the present invention and also referred to as the first invention.

Preferably, the trans-prenyltransferase (tPT) family protein contains, at positions 183 to 187 in the amino acid sequence of HbSDS from *Hevea brasiliensis* represented by SEQ ID NO:2 or at corresponding positions,
the following amino acid sequence (A1):

$$DDX_1X_2D \tag{A1}$$

wherein $X_1$ and $X_2$ are the same as or different from each other and each represent any amino acid residue, or
the following amino acid sequence (A2):

$$DDX_1X_2X_3X_4D \tag{A2}$$

wherein $X_1$, $X_2$, $X_3$, and $X_4$ are the same as or different from each other and each represent any amino acid residue, and
the trans-prenyltransferase (tPT) family protein contains, at positions 310 to 314 in the amino acid sequence of HbSDS from *Hevea brasiliensis* represented by SEQ ID NO:2 or at corresponding positions,
the following amino acid sequence (B):

$$DDX_{11}X_{12}D \tag{B}$$

wherein $X_{11}$ and $X_{12}$ are the same as or different from each other and each represent any amino acid residue.

Preferably, the gene coding for a trans-prenyltransferase (tPT) family protein is derived from a plant.

Preferably, the gene coding for a trans-prenytransferase (tPT) family protein is derived from a rubber-producing plant.

Preferably, the gene coding for a trans-prenyltransferase (tPT) family protein is derived from *Hevea brasiliensis*.

Preferably, the binding includes performing protein synthesis in the presence of both rubber particles and a cell-free protein synthesis solution containing an mRNA coding for a trans-prenyltransferase (tPT) family protein to bind the tPT family protein to the rubber particles.

Preferably, the cell-free protein synthesis solution contains a germ extract.

Preferably, the germ extract is derived from wheat.

Preferably, the rubber particles are present in the cell-free protein synthesis solution at a concentration of 5 to 50 g/L.

The first invention is also directed to a method for producing a pneumatic tire, the method including: kneading a trans-polyisoprenoid produced by the method for producing a trans-polyisoprenoid of the first invention with an additive to obtain a kneaded mixture; building a green tire from the kneaded mixture; and vulcanizing the green tire.

The first invention is also directed to a method for producing a rubber product, the method including: kneading a trans-polyisoprenoid produced by the method for producing a trans-polyisoprenoid of the first invention with an additive to obtain a kneaded mixture; forming a raw rubber product from the kneaded mixture; and vulcanizing the raw rubber product.

The present invention also relates to a vector, including: a promoter having a promoter activity that drives laticifer-specific gene expression; and a gene coding for a trans-prenyltransferase (tPT) family protein functionally linked to the promoter. This invention is hereinafter called the second aspect of the present invention and also referred to as the second invention.

Preferably, the promoter having a promoter activity that drives laticifer-specific gene expression is at least one selected from the group consisting of a promoter of a gene coding for rubber elongation factor (REF), a promoter of a gene coding for small rubber particle protein (SRPP), a promoter of a gene coding for Hevein 2.1 (HEV2.1), and a promoter of a gene coding for MYC1 transcription factor (MYC1).

The second invention is also directed to a transgenic plant into which any one of the above-described vectors has been introduced.

The second invention is also directed to a method for enhancing trans-isoprenoid production in a plant by introducing any one of the above-described vectors into the plant.

The second invention is also directed to a method for enhancing trans-polyisoprenoid production in a plant by introducing any one of the above-described vectors into the plant.

The second invention is also directed to a method for producing a pneumatic tire, the method including: kneading a trans-polyisoprenoid produced by a transgenic plant with an additive to obtain a kneaded mixture, the transgenic plant being produced by introducing any one of the above-described vectors into a plant; building a green tire from the kneaded mixture; and vulcanizing the green tire.

The second invention is also directed to a method for producing a rubber product, the method including: kneading a trans-polyisoprenoid produced by a transgenic plant with an additive to obtain a kneaded mixture, the transgenic plant being produced by introducing any one of the above-described vectors into a plant; forming a raw rubber product from the kneaded mixture; and vulcanizing the raw rubber product.

Advantageous Effects of Invention

The method for producing a trans-polyisoprenoid of the first invention includes binding a protein expressed from a gene coding for a trans-prenyltransferase (tPT) family protein to rubber particles in vitro. Thus, by binding a tPT family protein to rubber particles, trans rubber can be synthesized in the rubber particles, and therefore it is possible to efficiently produce trans rubber in reaction vessels (e.g., test tubes, industrial plants).

The method for producing a pneumatic tire of the first invention includes kneading a trans-polyisoprenoid produced by the method for producing a trans-polyisoprenoid of the first invention with an additive to obtain a kneaded mixture; building a green tire from the kneaded mixture; and vulcanizing the green tire. With this method, which produces a pneumatic tire from a trans-polyisoprenoid obtained by a highly efficient polyisoprenoid production method, it is possible to use plant resources effectively to produce environmentally friendly pneumatic tires.

The method for producing a rubber product of the first invention includes kneading a trans-polyisoprenoid produced by the method for producing a trans-polyisoprenoid of the first invention with an additive to obtain a kneaded mixture; forming a raw rubber product from the kneaded mixture; and vulcanizing the raw rubber product. With this method, which produces a rubber product from a trans-polyisoprenoid obtained by a highly efficient polyisoprenoid production method, it is possible to use plant resources effectively to produce environmentally friendly rubber products.

The vector of the second invention includes a promoter having a promoter activity that drives laticifer-specific gene expression and a gene coding for a trans-prenyltransferase (tPT) family protein functionally linked to the promoter. By introducing the vector into a plant, the gene coding for a protein involved in trans-polyisoprenoid biosynthesis in the vector can be expressed specifically in laticifers, thereby enhancing trans-isoprenoid or trans-polyisoprenoid production in the plant.

The method for producing a pneumatic tire of the second invention includes kneading a trans-polyisoprenoid produced by a transgenic plant with an additive to obtain a kneaded mixture, the transgenic plant being produced by introducing the vector of the second invention into a plant; building a green tire from the kneaded mixture; and vulcanizing the green tire. With this method, which produces a pneumatic tire from a trans-polyisoprenoid produced by a transgenic plant with an enhanced trans-polyisoprenoid production, it is possible to use plant resources effectively to produce environmentally friendly pneumatic tires.

The method for producing a rubber product of the second invention includes kneading a trans-polyisoprenoid produced by a transgenic plant with an additive to obtain a kneaded mixture, the transgenic plant being produced by introducing the vector of the second invention into a plant; forming a raw rubber product from the kneaded mixture; and vulcanizing the raw rubber product. With this method, which produces a pneumatic tire from a trans-polyisoprenoid produced by a transgenic plant with an enhanced trans-polyisoprenoid production, it is possible to use plant resources effectively to produce environmentally friendly rubber products.

DESCRIPTION OF EMBODIMENTS

Herein, the first invention and the second invention are also referred to collectively as the present invention. The first invention will be described first, and the second invention will be described later.

First Invention

The method for producing a trans-polyisoprenoid of the first invention includes binding a protein expressed from a gene coding for a tram-prenyltransferase (tPT) family protein to rubber particles in vitro.

Figure 1:
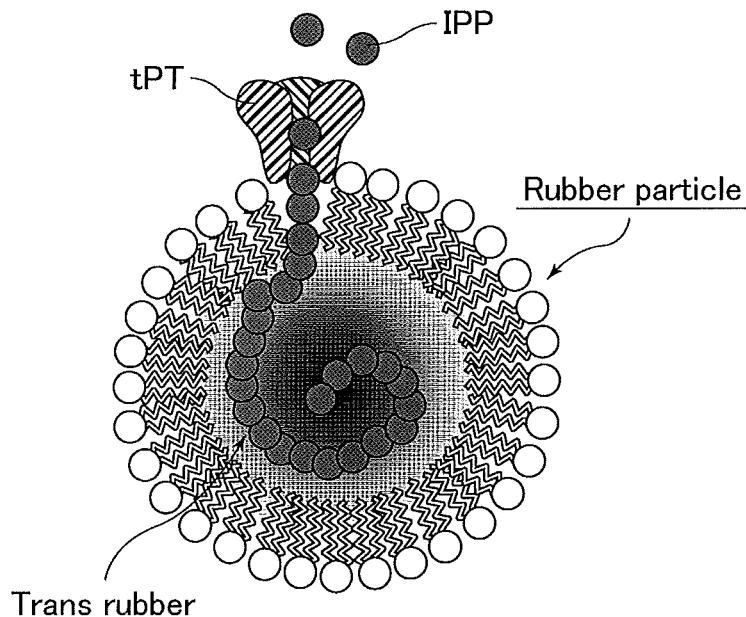
FIG. 1 is a presumptive diagram illustrating rubber synthesis by tPT on a rubber particle.

The inventors were the first to discover that a trans-polyisoprenoid (trans rubber) can be synthesized by binding a tPT family protein to rubber particles in vitro. It is presumed that tPT family proteins are disposed on rubber particles to synthesize rubber as shown in FIG. 1. FIG. 1 schematically illustrates an exemplary synthesis of trans rubber within a rubber particle by polymerization of an isopentenyl diphosphate (IPP) substrate by a tPT family protein depicted as tPT. Thus, by binding a tPT family protein to rubber particles in vitro, for example in a reaction vessel (e.g., a test tube or industrial plant) as in the production method of the first invention, a trans-polyisoprenoid (trans rubber) can be synthesized in the rubber particles, and therefore it is possible to efficiently produce trans rubber in a reaction vessel (e.g., a test tube or industrial plant).

The production method of the first invention may include any other step as long as it involves the above binding step, and each step may be performed once or repeated multiple times.

The amount of the tPT family protein to be bound to the rubber particles is not particularly limited in the first invention.

Herein, the expression "binding a tPT family protein to rubber particles" means that, for example, the tPT family protein is fully or partially incorporated into the rubber particles or inserted into the membrane structure of the rubber particles. It is not limited to these embodiments and also includes embodiments in which, for example, the tPT family protein is localized on the surface or inside of the rubber particles. Moreover, the concept of binding to rubber particles also includes embodiments in which the tPT family protein forms a complex with another protein bound to the rubber particles to exist in the form of the complex on the rubber particles.

A supplementary description of the present invention is given below.

First, for example, even if it were known that cis-natural rubber could be synthesized by binding rubber particles to a cis-prenyltranspherase (CPT) family protein which is considered to be deeply involved in the biosynthesis of cis-natural rubber, a person skilled in the art, in light of the experimental results of the CPT family protein, would not attempt to simply change the CPT family protein to a tPT family protein because tPT family proteins and CPT family proteins belong to very different protein families and have very different protein structures.

Furthermore, since tPT family proteins are not present on rubber particles in vivo, particularly in rubber-producing plants capable of producing cis-natural rubber, a person skilled in the art has no motivation to bind a tPT family protein to rubber particles. If a skilled person were to consider biding a tPT family protein to rubber particles, the skilled person, who knows the above fact, could not predict at all that the binding of a tPT family protein to rubber particles would lead to rubber synthesis.

In such circumstances, it has been found that binding a tPT family protein to rubber particles enables synthesis of a trans-polyisoprenoid (trans rubber) in the rubber particles. Thus, this is considered a surprising result which could not have been predicted by one skilled in this art.

The origin of the rubber particles is not particularly limited. For example, the rubber particles may be derived from the latex of a rubber-producing plant such as *Hevea brasiliensis, Taraxacum kok-saghyz, Parthenium argentatum, Sonchus oleraceus*, or *Ficus elastica*.

The particle size of the rubber particles is also not particularly limited. Rubber particles having a predetermined particle size may be sorted out and used, or a mixture of rubber particles having different particle sizes may be used. When rubber particles having a predetermined particle size are sorted out and used, the rubber particles may be either small rubber particles (SRP) having a small particle size or large rubber particles (LRP) having a large particle size.

In order to sort out the rubber particles having a predetermined particle size, commonly used methods may be used, including, for example, methods which involve centrifugation, preferably multistage centrifugation. A specific method includes centrifugation at 500-1500×g, centrifugation at 1700-2500×g, centrifugation at 7000-9000×g, centrifugation at 15000-25000×g, and centrifugation at 40000-60000×g, carried out in that order. The duration of each centrifugation treatment is preferably 20 minutes or longer, more preferably 30 minutes or longer, still more preferably 40 minutes or longer, but is preferably 120 minutes or shorter, more preferably 90 minutes or shorter. The temperature for each centrifugation treatment is preferably 0 to 10° C., more preferably 2 to 8° C., particularly preferably 4° C.

In the binding step, a protein expressed from a gene coding for a trans-prenyltransferase (tPT) family protein is bound to rubber particles in vitro.

The origin of the gene coding for a trans-prenyltransferase (tPT) family protein is not particularly limited. The gene may be derived from a microorganism, an animal, or a plant, preferably a plant, more preferably a rubber-producing plant, still more preferably at least one selected from the group consisting of plants of the genera *Hevea*, *Sonchus*, *Taraxacum*, and *Parthenium*. In particular, it is further preferably derived from at least one species of plant selected from the group consisting of *Hevea brasiliensis*, *Sonchus oleraceus*, *Parthenium argentatum*, and *Taraxacum kok-saghyz*, particularly preferably from *Hevea brasiliensis*.

The plant is not particularly limited, and examples include *Hevea* species such as *Hevea brasiliensis*; *Sonchus* species such as *Sonchus oleraceus*, *Sonchus asper*, and *Sonchus brachyotus*; *Solidago* species such as *Solidago altissima*, *Solidago virgaurea* subsp. *asiatica*, *Solidago virgaurea* subsp. *leipcarpa*, *Solidago virgaurea* subsp. *leipcarpa* f. *paludosa*, *Solidago virgaurea* subsp. *gigantea*, and *Solidago gigantea* Ait. var. *leiophylla* Fernald; *Helianthus* species such as *Helianthus annus*, *Helianthus argophyllus*, *Helianthus atrorubens*, *Helianthus debilis*, *Helianthus decapetalus*, and *Helianthus giganteus*; *Taraxacum* species such as dandelion (*Taraxacum*), *Tararacum venustum* H. Koidz, *Taraxacum hondoense* Nakai, *Taraxacum platycarpum* Dahlst, *Taraxacum japonicum*, *Taraxacum officinale* Weber, *Taraxacum kok-saghyz*, and *Taraxacum brevicorniculatum*; *Ficus* species such as *Ficus carica*, *Ficus elastica*, *Ficus pumila* L., *Ficus erecta* Thumb., *Ficus ampelas* Burm. f, *Ficus benguetensis* Merr., *Ficus irisana* Elm., *Ficus microcarpa* L. f., *Ficus septica* Burm. f., and *Ficus benghalensir*, *Parthenium* species such as *Parthenium argentatum*, *Parthenium hysterophorus*, and *Ambrosia artemisiifolia* (*Parthenium hysterophorus*); lettuce (*Lactuca sativa*); *Ficus benghalensis*; *Arabidopsis thaliana*; and *Eucommia ulmoides*.

Figure 2:
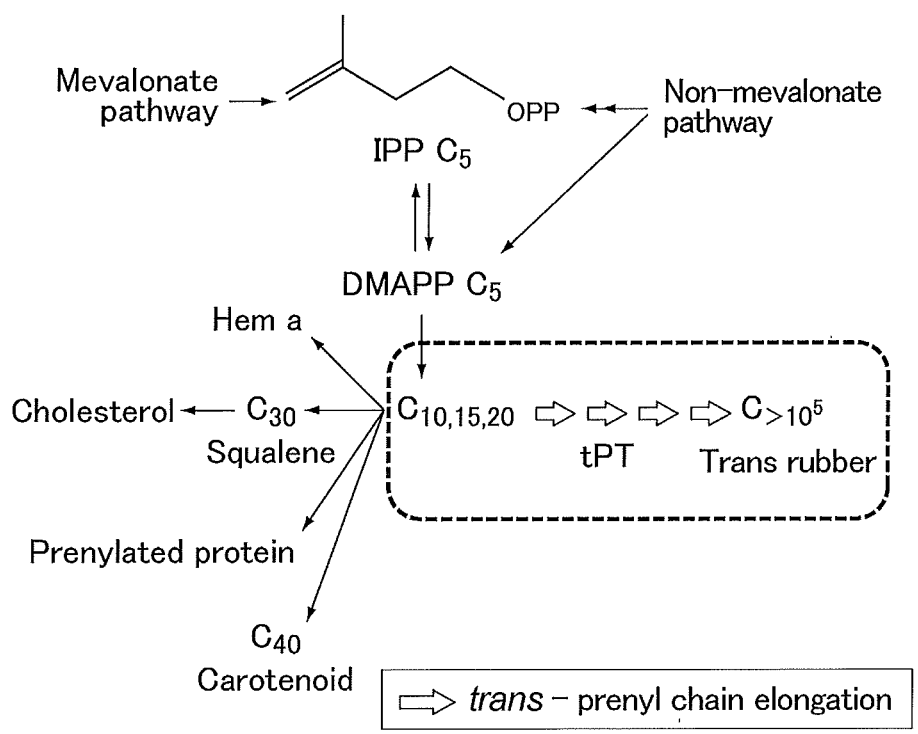
FIG. 2 is a schematic diagram illustrating part of a trans-polyisoprenoid biosynthesis pathway.

Herein, the term "trans-prenyltransferase (tPT) family protein" refers to an enzyme that catalyzes a reaction of trans-chain elongation of an isoprenoid compound. Specifically, for example, in plants, trans-polyisoprenoids are biosynthesized via trans-polyisoprenoid biosynthesis pathways as shown in FIG. 2, in which tPT family proteins are considered to be enzymes that catalyze the reactions enclosed by the dotted frame in FIG. 2. The tPT family proteins are characterized by having an amino acid sequence contained in the trans-IPPS HT domain (NCBI Accession No. cd00685).

Herein, the term "isoprenoid compound" refers to a compound containing an isoprene unit ($C_5H_8$). The term "trans-isoprenoid" refers to a compound including an isoprenoid compound in which isoprene units are trans-linked (in particular, the content of trans bonds is preferably at least 90%, more preferably at least 95%, still more preferably at least 97% of the total bonds), and examples include trans-polyisoprenoids (trans rubber) such as farnesyl diphosphate, geranylgeranyl diphosphate, hexaprenyl diphosphate, heptaprenyl diphosphate, and trans-1,4-polyisoprene.

Figure 5:
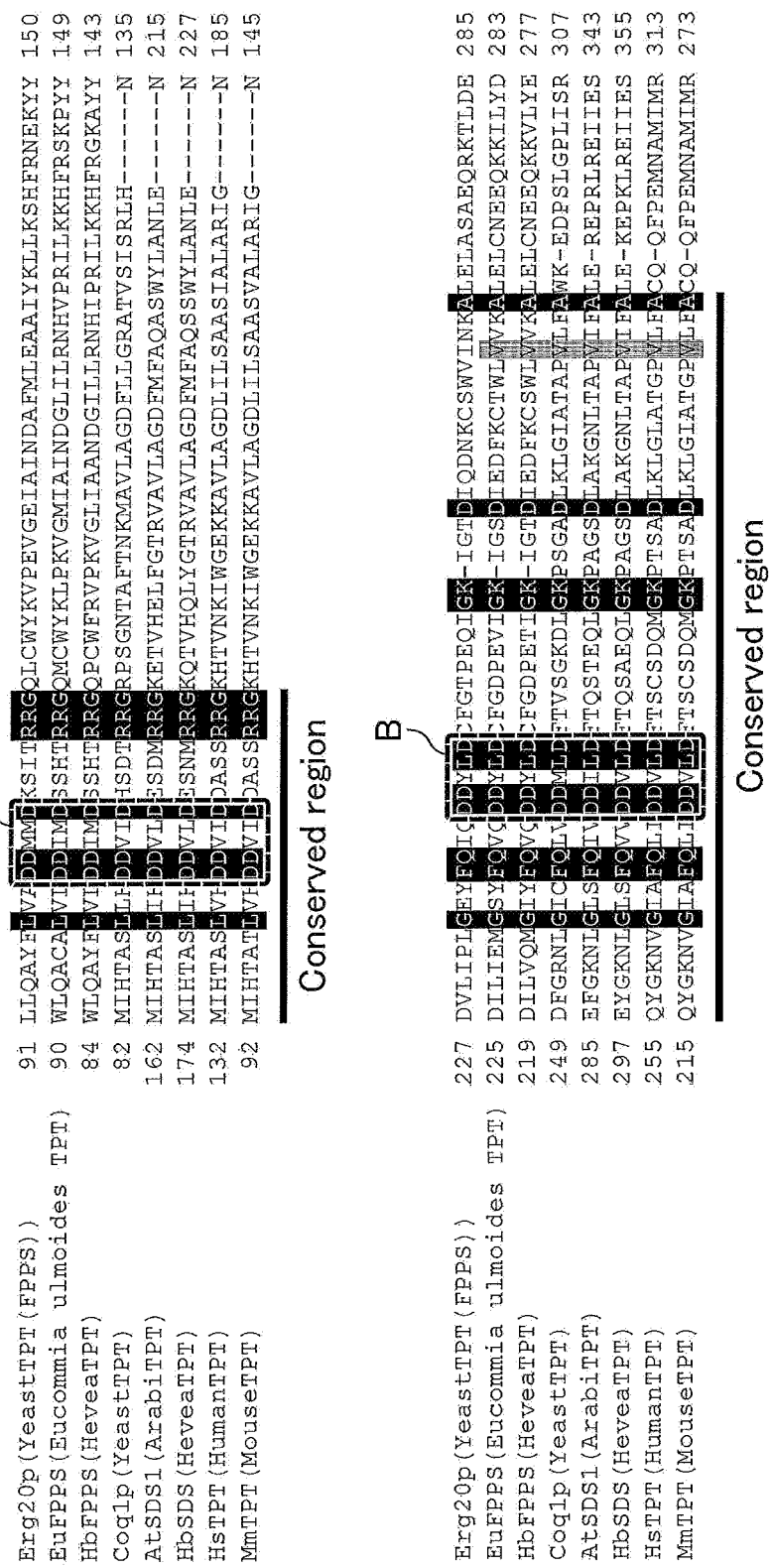
FIG. 5 is an outline diagram illustrating the results of multiple sequence alignment of tPT family proteins derived from various organisms.

FIG. 5 is an outline diagram illustrating the results of multiple sequence alignment of tPT family proteins derived from various organisms. According to literature, such as Andrew H.-J. Wang et al., Eur. J. Biochem. 269, pp. 3339-3354 (2002), box A (corresponding to positions 183 to 187 of HbSDS from *Hevea brasiliensis* represented by SEQ ID NO:2) and box B (corresponding to positions 310 to 314 of HbSDS from *Hevea brasiliensis* represented by SEQ ID NO:2) in FIG. 5 are parts of highly conserved regions of tPT family proteins derived from various organisms. The term "conserved region" refers to a site having a similar sequence (structure) which is presumed to have a similar protein function. In particular, it is considered that an amino acid sequence at positions corresponding to positions 183 to 187 of HbSDS from *Hevea brasiliensis* represented by SEQ ID NO:2, and an amino acid sequence at positions corresponding to positions 310 to 314 of HbSDS from *Hevea brasiliensis* represented by SEQ ID NO:2 are conserved as specific motifs, and proteins having these motifs at the respective positions have the functions of tPT family proteins.

The multiple sequence alignment can be carried out as described later in EXAMPLES.

Specifically, the trans-prenyltransferase (tPT) family protein preferably contains, at positions 183 to 187 in the amino acid sequence of HbSDS from *Hevea brasiliensis* represented by SEQ ID NO:2 or at corresponding positions, the following amino acid sequence (A1):

$$DDX_1X_2D \tag{A1}$$

wherein $X_1$ and $X_2$ are the same as or different from each other and each represent any amino acid residue, or the following amino acid sequence (A2):

$$DDX_1X_2X_3X_4D \tag{A2}$$

wherein $X_1$, $X_2$, $X_3$, and $X_4$ are the same as or different from each other and each represent any amino acid residue, and
    the trans-prenyltransferase (tPT) family protein contains, at positions 310 to 314 in the amino acid sequence of HbSDS from *Hevea brasiliensis* represented by SEQ ID NO:2 or at corresponding positions, the following amino acid sequence (B):

$$DDX_{11}X_{12}D \tag{B}$$

wherein $X_{11}$ and $X_{12}$ are the same as or different from each other and each represent any amino acid residue. As described above, the tPT family protein having such a sequence is considered to have the functions of tPT family proteins, including the function as an enzyme that catalyzes a reaction of trans-chain elongation of an isoprenoid compound. By binding this tPT family protein to rubber particles, it is possible to synthesize trans rubber in the rubber particles.

The tPT family protein preferably contains, at positions 183 to 187 in the amino acid sequence of HbSDS from *Hevea brasiliensis* represented by SEQ ID NO:2 or at corresponding positions, the following amino acid sequence (A1):

$$DDX_1X_2D \tag{A1}$$

wherein $X_1$ and $X_2$ are the same as or different from each other and each represent any amino acid residue, or the following amino acid sequence (A2):

$$DDX_1X_2X_3X_4D \tag{A2}$$

wherein $X_1$, $X_2$, $X_3$, and $X_4$ are the same as or different from each other and each represent any amino acid residue. More preferably, in the amino acid sequences (A1) and (A2), $X_1$ denotes M, I, or V, and $X_2$ denotes M, I, or L.

The tPT family protein contains, at positions 310 to 314 in the amino acid sequence of HbSDS from *Hevea brasiliensis* represented by SEQ ID NO:2 or at corresponding positions, the following amino acid sequence (B):

$$DDX_{11}X_{12}D \quad (B)$$

wherein $X_{11}$ and $X_{12}$ are the same as or different from each other and each represent any amino acid residue. More preferably, in the amino acid sequence (B), $X_{11}$ denotes Y, M, I, or V, and $X_{12}$ denotes L.

Specifically, the conserved region corresponding to positions 183 to 187 of HbSDS from *Hevea brasiliensis* represented by SEQ ID NO:2 corresponds for example to:
- positions 100 to 104 of FPPS from yeast represented by SEQ ID NO:3;
- positions 99 to 103 of EuFPPS from *Eucommia ulmoides* represented by SEQ ID NO:4;
- positions 93 to 97 of HbFPPS from *Hevea brasiliensis* represented by SEQ ID NO:5;
- positions 91 to 95 of TPT from yeast represented by SEQ ID NO:6;
- positions 171 to 175 of AtSDS1 from *Arabidopsis thaliana* represented by SEQ ID NO:7;
- positions 141 to 145 of HsTPT from human represented by SEQ ID NO:8; or
- positions 101 to 105 of MmTPT from mouse represented by SEQ ID NO:9.

The conserved region corresponding to positions 310 to 314 of HbSDS from *Hevea brasiliensis* represented by SEQ ID NO:2 corresponds for example to:
- positions 240 to 244 of FPPS from yeast represented by SEQ ID NO:3;
- positions 238 to 242 of EuFPPS from *Eucommia ulmoides* represented by SEQ ID NO:4;
- positions 232 to 236 of HbFPPS from *Hevea brasiliensis* represented by SEQ ID NO:5;
- positions 262 to 266 of TPT from yeast represented by SEQ ID NO:6;
- positions 298 to 302 of AtSDS1 from *Arabidopsis thaliana* represented by SEQ ID NO:7;
- positions 268 to 272 of HsTPT from human represented by SEQ ID NO:8; or
- positions 228 to 232 of MmTPT from mouse represented by SEQ ID NO:9.

Examples of the tPT family protein include: tPT derived from yeast, such as FPPS (Erg20p [*Saccharomyces cerevisiae* R103]) and TPT (Coq1p [*Saccharomyces cerevisiae* YJM1342]); tPT derived from *Eucommia ulmoides*, such as EuFPPS (farnesyl pyrophosphate synthetase [*Eucommia ulmoides*]); tPT derived from *Hevea brasiliensis*, such as HbFPPS (farnesyl diphosphate synthase [*Hevea brasiliensis*]) and HbSDS (solanesyl diphosphate synthase [*Hevea brasiliensis*]); tPT derived from *Arabidopsis thaliana*, such as AtSDS1 (solanesyl diphosphate synthase 1 [*Arabidopsis thaliana*]); tPT derived from human, such as HsTPT (trans-prenyltransferase [*Homo sapiens*]); and tPT derived from mouse, such as MmTPT (trans-prenyltransferase [*Mus musculus*]).

In addition to rubber-producing plants which produce rubber, other organisms such as plants, animals, and microorganisms have genes coding for the tPT family proteins. Of course the tPT family proteins from these organisms are naturally not involved in rubber synthesis. In spite of this, according to the present invention, trans rubber can be synthesized in rubber particles by binding any tPT family protein, regardless of the origin, type, and other factors of the protein, to the rubber particles. Thus, according to the present invention, trans rubber can be synthesized in rubber particles by using any tPT family protein, for example, regardless of whether the gene coding for the tPT family protein is derived from a rubber-producing plant or any other organism or whether it is naturally involved in rubber synthesis. This is strongly suggested by the mechanism (which indicates that the host to be transfected, or in other words the environment in which the cis-prenyltransferase (CPT) family protein is expressed is more important for rubber synthesis activity than the origin or type of the CPT family protein) already suggested in PCT/JP2016/069172 by the present inventors.

The tPT family protein used in the present invention desirably has a transmembrane domain on the N-terminal side to have a higher affinity for rubber particles. In the case of a wild type having no transmembrane domain, a transmembrane domain may be artificially fused to the N-terminal side of the tPT family protein. The transmembrane domain to be fused may have any amino acid sequence, desirably an amino acid sequence of the transmembrane domain of a protein inherently bound to rubber particles in nature.

Specific examples of the tPT family protein include the following protein [1]:

[1] A Protein Having the Amino Acid Sequence Represented by SEQ ID NO:2.

Moreover, it is known that proteins having one or more amino acid substitutions, deletions, insertions, or additions relative to the original amino acid sequence can have the inherent function. Thus, another specific example of the tPT family protein is the following protein [2]:

[2] a protein having an amino acid sequence containing one or more amino acid substitutions, deletions, insertions, and/or additions relative to the amino acid sequence represented by SEQ ID NO:2, and having an enzyme activity that catalyzes a reaction of trans-chain elongation of an isoprenoid compound.

In order to maintain the function of the tPT family protein, the protein preferably has an amino acid sequence containing one or more, more preferably 1 to 83, still more preferably 1 to 62, further preferably 1 to 41, particularly preferably 1 to 20, most preferably 1 to 8, yet most preferably 1 to 4 amino acid substitutions, deletions, insertions, and/or additions relative to the amino acid sequence represented by SEQ ID NO:2.

Among other amino acid substitutions, conservative substitutions are preferred. Specific examples include substitutions within each of the following groups in the parentheses: (glycine, alanine), (valine, isoleucine, leucine), (aspartic acid, glutamic acid), (asparagine, glutamine), (serine, threonine), (lysine, arginine), and (phenylalanine, tyrosine).

It is also known that proteins with amino acid sequences having high sequence identity to the original amino acid sequence can also have similar functions. Thus, another specific example of the tPT family protein is the following protein [3]:

[3] a protein having an amino acid sequence with at least 80% sequence identity to the amino acid sequence represented by SEQ ID NO:2, and having an enzyme activity that catalyzes a reaction of trans-chain elongation of an isoprenoid compound.

In order to maintain the function of the tPT family protein, the sequence identity to the amino acid sequence represented by SEQ ID NO:2 is preferably at least 85%, more preferably at least 90%, still more preferably at least 95%, particularly preferably at least 98%, most preferably at least 99%.

Herein, the sequence identity between amino acid sequences or nucleotide sequences may be determined using the algorithm BLAST [Pro. Natl. Acad. Sci. USA, 90, 5873 (1993)] developed by Karlin and Altschul or FASTA [Methods Enzymol., 183, 63 (1990)].

Whether it is a protein having the above enzyme activity or not may be determined by conventional techniques, such as by expressing a target protein in a transformant produced by introducing a gene coding for the target protein into *Escherichia coli* or other host organisms, and analyzing the presence or absence of the function of the target protein by the corresponding activity measuring method.

The gene coding for the tPT family protein is not particularly limited as long as it codes for the tPT family protein to express and produce the tPT family protein. Specific examples of the gene include the following DNAs [1] and [2]:

[1] a DNA having the nucleotide sequence represented by SEQ ID NO:1; and

[2] a DNA which hybridizes under stringent conditions to a DNA having a nucleotide sequence complementary to the nucleotide sequence represented by SEQ ID NO:1, and which codes for a protein having an enzyme activity that catalyzes a reaction of trans-chain elongation of an isoprenoid compound.

Herein, the term "hybridize" means a process in which a DNA hybridizes to a DNA having a specific nucleotide sequence or a part of the DNA. Thus, the DNA having a specific nucleotide sequence or part of the DNA may have a nucleotide sequence long enough to be usable as a probe in Northern or Southern blot analysis or as an oligonucleotide primer in polymerase chain reaction (PCR) analysis. The DNA to be used as a probe may have a length of at least 100 bases, preferably at least 200 bases, more preferably at least 500 bases although it may be a DNA of at least 10 bases, preferably at least 15 bases.

Techniques to perform DNA hybridization experiments are well known. The hybridization conditions under which experiments are carried out may be determined in accordance with, for example, Molecular Cloning, 2nd ed. and 3rd ed. (2001), Methods for General and Molecular Bacteriology, ASM Press (1994), Immunology methods manual, Academic press (Molecular), and many other standard textbooks.

The stringent conditions may include, for example, an overnight incubation at 42° C. of a DNA-immobilized filter and a DNA probe in a solution containing 50% formamide, 5×SSC (750 mM sodium chloride, 75 mM sodium citrate), 50 mM sodium phosphate (pH 7.6), 5×Denhardt's solution, 10% V dextran sulfate, and 20 µg/L denatured salmon sperm DNA, followed by washing the filter for example in a 0.2×SSC solution at approximately 65° C. Less stringent conditions may also be used. Changes in stringency may be accomplished through the manipulation of formamide concentration (lower percentages of formamide result in lower stringency), salt concentrations or temperature. For example, low stringent conditions include an overnight incubation at 37° C. in a solution containing 6×SSCE (20×SSCE: 3 mol/L sodium chloride, 0.2 mol/L sodium dihydrogen phosphate, 0.02 mol/L EDTA, pH 7.4), 0.5% SDS, 30% formamide, and 100 µg/L denatured salmon sperm DNA, followed by washing in a 1×SSC solution containing 0.1% SDS at 50° C. In addition, to achieve even lower stringency, washes performed following hybridization may be done at higher salt concentrations (e.g. 5×SSC) in the above-mentioned low stringent conditions.

Variations in the above conditions may be accomplished through the inclusion or substitution of blocking reagents used to suppress background in hybridization experiments. The inclusion of blocking reagents may require modification of the hybridization conditions for compatibility.

The DNA capable of hybridization under stringent conditions as described above may have a nucleotide sequence with at least 80%, preferably at least 90%, more preferably at least 95%, still more preferably at least 98%, particularly preferably at least 99% sequence identity to the nucleotide sequence represented by SEQ ID NO:1 as calculated using a program such as BLAST or FASTA with the parameters mentioned above.

Whether the DNA which hybridizes to the aforementioned DNA under stringent conditions is a DNA coding for a protein having a predetermined enzyme activity or not may be determined by conventional techniques, such as by expressing a target protein in a transformant produced by introducing a gene coding for the target protein into *Escherichia coli* or other host organisms, and analyzing the presence or absence of the function of the target protein by the corresponding activity measuring method.

Conventional techniques may be employed to identify the amino acid sequence or nucleotide sequence of the protein. For example, total RNA is extracted from a growing plant, the mRNA is optionally purified, and a cDNA is synthesized by a reverse transcription reaction. Subsequently, degenerate primers are designed based on the amino acid sequence of a known protein corresponding to the target protein, a DNA fragment is partially amplified by RT-PCR, and the sequence is partially identified. Then, the full-length nucleotide sequence or amino acid sequence is identified, e.g. by the RACE method. The RACE method (rapid amplification of cDNA ends method) refers to a method in which, when the nucleotide sequence of a cDNA is partially known, PCR is performed based on the nucleotide sequence data of such a known region to clone an unknown region extending to the cDNA terminal. This method is capable of cloning full-length cDNA by PCR without preparing a cDNA library.

The degenerate primers may each preferably be prepared from a plant-derived sequence having a highly similar sequence part to the target protein.

If the nucleotide sequence coding for the protein is known, the full-length nucleotide sequence or amino acid sequence can be identified by designing a primer containing a start codon and a primer containing a stop codon using the known nucleotide sequence, followed by performing RT-PCR using a synthesized cDNA as a template.

In the binding step, additional proteins may further be bound to the rubber particles as long as the protein expressed from a gene coding for a trans-prenyltransferase (tPT) family protein is bound to the rubber particles in vitro.

The origin of the additional proteins is not particularly limited, but preferably the additional proteins are derived from any of the plants mentioned above, more preferably rubber-producing plants, still more preferably at least one selected from the group consisting of plants of the genera *Hevea*, *Sonchus*, *Taraxacum*, and *Parthenium*. In particular, they are further preferably derived from at least one species of plant selected from the group consisting of *Hevea brasiliensis*, *Sonchus oleraceus*, *Parthenium argentatum*, and *Taraxacum kok-saghyz*, particularly preferably from *Hevea brasiliensis*.

The additional proteins are not limited and may each be any protein, but in view of rubber synthesis activity of the rubber particles, they are each preferably a protein that inherently exists on rubber particles in a rubber-producing plant. The protein that exists on rubber particles may be a protein bound to a large part of the membrane surface of rubber particles, or a protein inserted into and bound to the membrane of rubber particles, or a protein that forms a complex with another protein bound to the membrane to exist on the membrane surface.

Examples of the protein that inherently exists on rubber particles in a rubber-producing plant include Nogo-B receptor (NgBR), rubber elongation factor (REF), small rubber particle protein (SRPP), β-1,3-glucanase, and Hevein.

The binding step may be carried out by any method that can bind a tPT family protein to rubber particles in vitro, such as, for example, by performing protein synthesis in the presence of both rubber particles and a cell-free protein synthesis solution containing an mRNA coding for a tPT family protein to bind the tPT family protein to the rubber particles.

The binding step preferably includes performing protein synthesis in the presence of both rubber particles and a cell-free protein synthesis solution containing an mRNA coding for a tPT family protein to bind the tPT family protein to the rubber particles, among other methods.

In other words, it is preferred to obtain rubber particles bound to a tPT family protein by performing protein synthesis in the presence of both rubber particles and a cell-free protein synthesis solution containing an mRNA coding for the tPT family protein (more specifically, using a mixture of rubber particles with a cell-free protein synthesis solution containing an mRNA coding for the tPT family protein).

Since liposomes are artificially produced as lipid bilayer membranes formed of phospholipids, glyceroglycolipids, cholesterol, or other components, no protein is bound to the surface of the produced liposomes. In contrast, although rubber particles collected from the latex of rubber-producing plants are also coated with a lipid membrane, the membrane of the rubber particles is a naturally derived membrane in which proteins that have been synthesized in the plants are already bound to the surface of the membrane. In view of this, it is expected to be more difficult to bind an additional protein to rubber particles that are already bound to and coated with proteins than to bind it to liposomes not bound to any protein. There is also concern that the proteins already bound to rubber particles could inhibit cell-free protein synthesis. For these reasons, difficulties have been anticipated in performing cell-free protein synthesis in the presence of rubber particles. Under such circumstances, the present inventors have conducted cell-free synthesis of a tPT family protein in the presence of rubber particles, which had never been attempted in the past, and it has been found that with this method, it is possible to produce rubber particles bound to a tPT family protein.

The protein synthesis in the presence of both rubber particles and a cell-free protein synthesis solution containing an mRNA coding for a tPT family protein is namely the synthesis of a tPT family protein by cell-free protein synthesis, and the synthesized tPT family protein maintains its biological function (native state). As the cell-free protein synthesis is performed in the presence of rubber particles, the synthesized tPT family protein in its native state can be bound to the rubber particles.

The binding of a tPT family protein to rubber particles by protein synthesis in the presence of both the cell-free protein synthesis solution and the rubber particles means that, for example, each tPT family protein synthesized by the protein synthesis is fully or partially incorporated into the rubber particles or inserted into the membrane structure of the rubber particles. It is not limited to these embodiments and also includes, for example, embodiments in which the protein is localized on the surface or inside of the rubber particles. Moreover, the concept of binding to rubber particles also includes embodiments in which the protein forms a complex with another protein bound to the rubber particles as described above to exist in the form of the complex on the rubber particles.

Each mRNA coding for a tPT family protein serves as a translation template that can be translated to synthesize the tPT family protein.

The origin of the mRNA coding for a tPT family protein is not particularly limited, and the mRNA may be derived from a microorganism, an animal, or a plant, preferably a plant, more preferably any of the plants mentioned above, still more preferably a rubber-producing plant, further preferably at least one selected from the group consisting of plants of the genera *Hevea Sonchus, Taraxacum*, and *Parthenium*. In particular, it is especially preferably derived from at least one species of plant selected from the group consisting of *Hevea brasiliensis, Sonchus oleraceus, Parthenium argentatum*, and *Taraxacum kok-saghyz*, most preferably from *Hevea brasiliensis*.

The mRNA coding for a tPT family protein may be prepared by any method as long as the prepared mRNA serves as a translation template that can be translated to synthesize the tPT family protein. For example, the mRNA may be prepared by extracting total RNA from the latex of a rubber-producing plant by, for example, the hot phenol method, synthesizing cDNA from the total RNA, obtaining a DNA fragment of a gene coding for a tPT family protein using primers prepared based on the nucleotide sequence data of the gene coding for a tPT family protein, and performing an ordinary in vitro transcription reaction of the DNA fragment.

As long as the cell-free protein synthesis solution contains the mRNA coding for a tPT family protein, it may contain mRNAs coding for additional proteins.

The mRNAs coding for additional proteins may be ones that can be translated to express the additional proteins. The additional proteins may be as described above.

In the binding step in the first invention, cell-free synthesis of a tPT family protein is preferably performed in the presence of rubber particles. The cell-free protein synthesis may be carried out using the cell-free protein synthesis solution in a similar manner to conventional methods. The cell-free protein synthesis system used may be a common cell-free protein synthesis means, such as rapid translation system RTS500 (Roche Diagnostics); or wheat germ extracts prepared in accordance with Proc. Natl. Acad. Sci. USA, 97:559-564 (2000), JP 2000-236896 A, JP 2002-125693 A, and JP 2002-204689 A, or cell-free protein synthesis systems using the wheat germ extracts (JP 2002-204689 A, Proc. Natl. Acad. Sci. USA, 99:14652-14657 (2002)). Systems using germ extracts are preferred among these. Thus, in another suitable embodiment of the first invention, the cell-free protein synthesis solution contains a germ extract.

The source of the germ extract is not particularly limited. From the standpoint of translation efficiency, it is preferred to use a plant-derived germ extract for cell-free protein synthesis of a plant protein. It is particularly preferred to use a wheat-derived germ extract. Thus, in another suitable embodiment of the first invention, the germ extract is derived from wheat.

The method for preparing the germ extract is not particularly limited, and may be carried out conventionally, as described in, for example, JP 2005-218357 A.

The cell-free protein synthesis solution preferably further contains a cyclic nucleoside monophosphate derivative or a salt thereof (hereinafter, also referred to simply as "activity enhancer"). Protein synthesis activity can be further enhanced by the inclusion of the activity enhancer.

The cyclic nucleoside monophosphate derivative or salt thereof is not particularly limited as long as it can enhance cell-free protein synthesis activity. Examples include adenosine-3',5'-cyclic monophosphoric acid and its salts; adenosine-3',5'-cyclic monophosphorothioic acid (Sp-isomer) and its salts; adenosine-3',5'-cyclic monophosphorothioic acid (Rp-isomer) and its salts; guanosine-3',5'-cyclic monophosphoric acid and its salts; guanosine-3',5'-cyclic monophosphorothioic acid (Sp-isomer) and its salts; guanosine-3',5'-cyclic monophosphorothioic acid (Rp-isomer) and its salts; 8-bromoadenosine-3',5'-cyclic monophosphoric acid (bromo-cAMP) and its salts; 8-(4-chlorophenyl-thio)adenosine-3',5'-cyclic monophosphoric acid (chlorophenylthio-cAMP) and its salts; 5,6-dichloro-1-β-D-ribofuranosylbenzimidazole adenosine-3',5'-cyclic monophosphoric acid (dichlororibofuranosylbenzimidazole cAMP) and its salts; adenosine-2',5'-cyclic monophosphoric acid and its salts; adenosine-2',5'-cyclic monophosphorothioic acid (Sp-isomer) and its salts; adenosine-2',5'-cyclic monophosphorothioic acid (Rp-isomer) and its salts; guanosine-2',5'-cyclic monophosphoric acid and its salts; guanosine-2',5'-cyclic monophosphorothioic acid (Sp-isomer) and its salts; and guanosine-2',5'-cyclic monophosphorothioic acid (Rp-isomer) and its salts.

The base that forms a salt with the cyclic nucleoside monophosphate derivative is not particularly limited as long as it is biochemically acceptable and forms a salt with the derivative. Preferred are, for example, alkali metal atoms such as sodium or potassium, and organic bases such as tris-hydroxyaminomethane, among others.

Of these activity enhancers, adenosine-3',5'-cyclic monophosphoric acid or adenosine-3',5'-cyclic monophosphate sodium salt is particularly preferred. These activity enhancers may be used alone or in combinations of two or more.

The activity enhancer may be added to the cell-free protein synthesis solution in advance. If the activity enhancer is unstable in the solution, it is preferably added during the protein synthesis reaction performed in the presence of both the cell-free protein synthesis solution and rubber particles.

The amount of the activity enhancer added is not particularly limited as long as the activity enhancer is at a concentration that can activate (increase) the protein synthesis reaction in the cell-free protein synthesis solution. Specifically, the final concentration in the reaction system may usually be at least 0.1 millimoles/liter. The lower limit of the concentration is preferably 0.2 millimoles/liter, more preferably 0.4 millimoles/liter, particularly preferably 0.8 millimoles/liter, while the upper limit of the concentration is preferably 24 millimoles/liter, more preferably 6.4 millimoles/liter, particularly preferably 3.2 millimoles/liter.

The temperature of the cell-free protein synthesis solution to which the activity enhancer is added is not particularly limited, but is preferably 0 to 30° C., more preferably 10 to 26° C.

In addition to the mRNA (translation template) coding for a tPT family protein, the cell-free protein synthesis solution also contains ATP, GTP, creatine phosphate, creatine kinase, l-amino acids, potassium ions, magnesium ions, and other components required for protein synthesis, and optionally an activity enhancer. Such a cell-free protein synthesis solution can serve as a cell-free protein synthesis reaction system.

Since the germ extract prepared as described in JP 2005-218357 A contains tRNA in an amount necessary for protein synthesis reaction, addition of separately prepared tRNA is not required when the germ extract prepared as above is used in the cell-free protein synthesis solution. In other words, tRNA may be added to the cell-free protein synthesis solution, if necessary.

The binding step in the first invention preferably includes performing protein synthesis in the presence of both rubber particles and a cell-free protein synthesis solution containing an mRNA coding for a tPT family protein. Specifically, this can be accomplished by adding rubber particles to the cell-free protein synthesis solution at a suitable point either before or after protein synthesis, preferably before protein synthesis.

The rubber particles are preferably present in the cell-free protein synthesis solution at a concentration of 5 to 50 g/L. In other words, 5 to 50 g of rubber particles are preferably present in 1 L of the cell-free protein synthesis solution. If the concentration of rubber particles present in the cell-free protein synthesis solution is less than 5 g/L, a rubber layer may not be formed by separation treatment (e.g., ultracentrifugation) for collecting the rubber particles bound to the synthesized tPT family protein, and therefore it may be difficult to collect the rubber particles bound to the synthesized tPT family protein. Moreover, if the concentration of rubber particles present in the cell-free protein synthesis solution exceeds 50 g/L, the rubber particles may coagulate, so that the synthesized tPT family protein may fail to bind well to the rubber particles. The concentration of rubber particles is more preferably 10 to 40 g/L, still more preferably 15 to 35 g/L, particularly preferably 15 to 30 g/L.

In the protein synthesis in the presence of both rubber particles and the cell-free protein synthesis solution, additional rubber particles may be appropriately added as the reaction progresses. The cell-free protein synthesis solution and rubber particles are preferably present together during the period when the cell-free protein synthesis system is active, such as 3 to 48 hours, preferably 3 to 30 hours, more preferably 3 to 24 hours after the addition of rubber particles to the cell-free protein synthesis solution.

The rubber particles do not have to be subjected to any treatment, e.g., pretreatment, before use in the binding step in the first invention, preferably before being combined with the cell-free protein synthesis solution. However, proteins may be removed from the rubber particles with a surfactant beforehand to increase the proportion of the tPT family protein desired to be bound by the method of the first invention, among the proteins present on the rubber particles. Thus, in another suitable embodiment of the first invention, the rubber particles used in the first invention are washed with a surfactant before use in the binding step in the first invention, preferably before being combined with the cell-free protein synthesis solution.

The surfactant is not particularly limited, and examples include nonionic surfactants and amphoteric surfactants. Nonionic or amphoteric surfactants, among others, are suitable because they have only a little denaturing effect on the proteins on the membrane, and amphoteric surfactants are especially suitable. Thus, in another suitable embodiment of the first invention, the surfactant is an amphoteric surfactant.

These surfactants may be used alone or in combinations of two or more.

Examples of the nonionic surfactants include polyoxyalkylene ether nonionic surfactants, polyoxyalkylene ester nonionic surfactants, polyhydric alcohol fatty acid ester nonionic surfactants, sugar fatty acid ester nonionic surfactants, alkyl polyglycoside nonionic surfactants, and polyoxyalkylene polyglucoside nonionic surfactants; and polyoxyalkylene alkylamines and alkyl alkanolamides.

Polyoxyalkylene ether or polyhydric alcohol fatty acid ester nonionic surfactants are preferred among these.

Examples of the polyoxyalkylene ether nonionic surfactants include polyoxyalkylene alkyl ethers, polyoxyalkylene alkylphenyl ethers, polyoxyalkylene polyol alkyl ethers, and polyoxyalkylene mono-, di- or tristyryl phenyl ethers. Among these, polyoxyalkylene alkylphenyl ethers are suitable. The "polyol" is preferably a C2-C12 polyhydric alcohol, such as ethylene glycol, propylene glycol, glycerin, sorbitol, glucose, sucrose, pentaerythritol, or sorbitan.

Examples of the polyoxyalkylene ester nonionic surfactants include polyoxyalkylene fatty acid esters and polyoxyalkylene alkyl rosin acid esters.

Examples of the polyhydric alcohol fatty acid ester nonionic surfactants include fatty acid esters of C2-C12 polyhydric alcohols and fatty acid esters of polyoxyalkylene polyhydric alcohols. More specific examples include sorbitol fatty acid esters, sorbitan fatty acid esters, glycerin fatty acid esters, polyglycerin fatty acid esters, and pentaerythritol fatty acid esters, as well as polyalkylene oxide adducts of the foregoing such as polyoxyalkylene sorbitan fatty acid esters and polyoxyalkylene glycerin fatty acid esters. Among these, sorbitan fatty acid esters are suitable.

Examples of the sugar fatty acid ester nonionic surfactants include fatty acid esters of sucrose, glucose, maltose, fructose, and polysaccharides, as well as polyalkylene oxide adducts of the foregoing.

Examples of the alkyl polyglycoside nonionic surfactants include those having, for example, glucose, maltose, fructose, or sucrose as the glycoside, such as alkyl glucosides, alkyl polyglucosides, polyoxyalkylene alkyl glucosides, and polyoxyalkylene alkyl polyglucosides, as well as fatty acid esters of the foregoing. Polyalkylene oxide adducts of any of the foregoing may also be used.

Examples of the alkyl groups in these nonionic surfactants include C4-C30 linear or branched, saturated or unsaturated alkyl groups. The polyoxyalkylene groups may have C2-C4 alkylene groups, and may have about 1 to 50 moles of added ethylene oxide, for example. Examples of the fatty acids include C4-C30 linear or branched, saturated or unsaturated fatty acids.

Of the nonionic surfactants, polyoxythyleneethylene (10) octylphenyl ether (Triton X-100) or sorbitan monolaurate (Span 20) is particularly preferred for their ability to moderately remove membrane-associated proteins while keeping the membrane of rubber particles stable and, further, having only a little denaturing effect on the proteins.

Examples of the amphoteric surfactants include zwitterionic surfactants such as quaternary ammonium salt group/sulfonate group ($-SO_3H$) surfactants, water-soluble quaternary ammonium salt group/phosphate group surfactants, water-insoluble quaternary ammonium salt group/phosphate group surfactants, and quaternary ammonium salt group/carboxyl group surfactants. The acid group in each of these zwitterionic surfactants may be a salt.

In particular, such a zwitterionic surfactant preferably has both positive and negative charges in a molecule. The acid dissociation constant (pKa) of the acid group is preferably 5 or less, more preferably 4 or less, still more preferably 3 or less.

Specific examples of the amphoteric surfactants include ammonium sulfobetaines such as 3-[(3-cholamidopropyl)dimethylamino]-2-hydroxy-1-propanesulfonate (CHAPSO), 3-[(3-cholamidopropyl)-dimethylamino]-propanesulfonate (CHAPS), N,N-bis(3-D-gluconamidopropyl)-cholamide, n-octadecyl-N,N'-dimethyl-3-amino-1-propanesulfonate, n-decyl-N,N'-dimethyl-3-amino-1-propanesulfonate, n-dodecyl-N,N'-dimethyl-3-amino-1-propanesulfonate, n-tetradecyl-N,N'-dimethyl-3-amino-1-propanesulfonate (Zwittergen™3-14), n-hexadecyl-N,N'-dimethyl-3-amino-1-propanesulfonate, and n-octadecyl-N,N'-dimethyl-3-amino-1-propanesulfonate; phosphocholines such as n-octylphosphocholine, n-nonylphosphocholine, n-decylphosphocholine, n-dodecylphosphocholine, n-tetradecylphosphocholine, and n-hexadecylphosphocholine; and phosphatidylcholines such as dilauroyl phosphatidylcholine, dimyristoyl phosphatidylcholine, dipalmitoyl phosphatidylcholine, distearoyl phosphatidylcholine, dioleoyl phosphatidylcholine, and dilinoleoyl phosphatidylcholine. Of these, 3-[(3-cholamidopropyl)dimethylamino]-propanesulfonate (CHAPS) is particularly preferred for its ability to moderately remove proteins while keeping the membrane of rubber particles stable.

The concentration of the surfactant for the treatment is preferably within three times the critical micelle concentration (CMC) of the surfactant used. The membrane stability of the rubber particles may be reduced if they are treated with the surfactant at a concentration exceeding three times the critical micelle concentration. The concentration is more preferably within 2.5 times, still more preferably within 2.0 times the CMC. The lower limit of the concentration is preferably at least 0.05 times, more preferably at least 0.1 times, still more preferably at least 0.3 times the CMC.

Examples of protein synthesis protein synthesis reaction systems or apparatuses for protein synthesis that can be used in the cell-free protein synthesis include a batch method (Pratt, J. M. et al., Transcription and Translation, Hames, 179-209, B. D. & Higgins, S. J., eds, IRL Press, Oxford (1984)), a continuous cell-free protein synthesis system in which amino acids, energy sources, and other components are supplied continuously to the reaction system (Spirin, A. S. et al., Science, 242, 1162-1164 (1988)), a dialysis method (Kigawa et al., 21st Annual Meeting of the Molecular Biology Society of Japan, WID 6), and an overlay method (instruction manual of PROTEIOS™ wheat germ cell-free protein synthesis core kit, Toyobo Co., Ltd.). Another method may be to supply template RNA, amino acids, energy sources, and other components, if necessary, to the protein synthesis reaction system, and discharge the synthesis product or decomposition product as required.

Among these, the dialysis method is preferred. The reason for this is as follows. The overlay method has the advantage of easy operation, but unfortunately rubber particles disperse in the reaction solution and thus are difficult to efficiently bind to the synthesized tPT family protein. In contrast, in the dialysis method, since the amino acids used as raw materials of the tPT family protein to be synthesized can pass through the dialysis membrane while rubber particles cannot pass therethrough, it is possible to prevent dispersal of rubber particles and thus to efficiently bind the synthesized tPT family protein to rubber particles.

The dialysis method refers to a method in which protein synthesis is carried out using the reaction solution for the cell-free protein synthesis as an internal dialysis solution, and an apparatus in which the internal dialysis solution is separated from an external dialysis solution by a dialysis membrane capable of mass transfer. Specifically, for example, a translation template is added to the synthesis reaction solution excluding the translation template, optionally after pre-incubation for an appropriate amount of time, and then the solution is put in an appropriate dialysis container as the internal reaction solution. Examples of the dialysis container include containers with a dialysis membrane attached to the bottom (e.g., Dialysis Cup 12,000 available from Daiichi Kagaku) and dialysis tubes (e.g., 12,000 available from Sanko Junyaku Co., Ltd.). The dialysis membrane used may have a molecular weight cutoff of 10,000 daltons or more, preferably about 12,000 daltons.

The external dialysis solution used may be a buffer containing amino acids. Dialysis efficiency can be increased by replacing the external dialysis solution with a fresh one when the reaction speed declines. The reaction temperature and time are selected appropriately according to the protein synthesis system used. For example, in the case of a system using a wheat-derived germ extract, the reaction may be carried out usually at 10 to 40° C., preferably 18 to 30° C., more preferably 20 to 26° C., for 10 minutes to 48 hours, preferably for 10 minutes to 30 hours, more preferably for 10 minutes to 24 hours.

Since the mRNA coding for a tPT family protein contained in the cell-free protein synthesis solution is easily broken down, the mRNA may be additionally added as appropriate during the protein synthesis reaction to make the protein synthesis more efficient. Thus, in another suitable embodiment of the first invention, the mRNA coding for a tPT family protein is additionally added during the protein synthesis reaction.

The addition time, the number of additions, the addition amount, and other conditions of the mRNA are not particularly limited, and may be selected appropriately.

In the production method of the first invention, the step of collecting the rubber particles may optionally be performed after the step of binding a protein expressed from a gene coding for a trans-prenyhransferase (tPT) family protein to rubber particles in vitro.

The rubber particle collection step may be carried out by any method that can collect the rubber particles. It may be carried out by conventional methods for collecting rubber particles. Specific examples include methods using centrifugation. When the rubber particles are collected by the centrifugation methods, the centrifugal force, centrifugation time, and centrifugation temperature may be selected appropriately so as to be able to collect the rubber particles. For example, the centrifugal force during the centrifugation is preferably 15000×g or more, more preferably 20000×g or more, still more preferably 25000×g or more. Moreover, since increasing the centrifugal force too much is not expected to produce a correspondingly high separation effect, the upper limit of the centrifugal force is preferably 50000×g or less, more preferably 45000×g or less. The centrifugation time is preferably at least 20 minutes, more preferably at least 30 minutes, still more preferably at least 40 minutes. Moreover, since increasing the centrifugation time too much is not expected to produce a correspondingly high separation effect, the upper limit of the centrifugation time is preferably 120 minutes or less, more preferably 90 minutes or less.

From the standpoint of maintaining the activity of the tPT family protein bound to the rubber particles, the centrifugation temperature is preferably 0 to 10° C., more preferably 2 to 8° C., particularly preferably 4° C.

For example, when the cell-free protein synthesis is performed, the rubber particles and the cell-free protein synthesis solution are separated into the upper and lower layers, respectively, by the centrifugation. The cell-free protein synthesis solution as the lower layer may then be removed to collect the rubber particles bound to the tPT family protein. The collected rubber particles may be re-suspended in an appropriate buffer with a neutral pH for storage.

The rubber particles collected by the rubber particle collection step can be used in the same way as usual natural rubber without the need for further special treatment.

Moreover, the trans-polyisoprenoid produced by the method for producing a trans-polyisoprenoid of the first invention can be recovered by subjecting the rubber particles to the solidification step described below.

The method for solidification in the solidification step is not particularly limited, and examples include a method of adding the rubber particles to a solvent that does not dissolve the trans-polyisoprenoid (trans rubber), such as ethanol, methanol, or acetone; and a method of adding an acid to the rubber particles. Rubber can be recovered as solids from the rubber particles by the solidification step. The obtained rubber may be dried if necessary before use.

Thus, according to the first invention, by binding a protein expressed from a gene coding for a trans-prenyltransferase (tPT) family protein to rubber particles in vitro, trans rubber can be synthesized in the rubber particles, and therefore it is possible to efficiently produce trans rubber (one example of trans-polyisoprenoid) in a reaction vessel (e.g., a test tube or industrial plant).

Thus, another aspect of the first invention relates to a method for synthesizing a trans-polyisoprenoid, which includes binding a protein expressed from a gene coding for a trans-prenyltransferase (tPT) family protein to rubber particles in vitro, for example in a reaction vessel (e.g., a test tube or industrial plant).

The step of binding a protein expressed from a gene coding for a trans-prenyltransferase (tPT) family protein to rubber particles in vitro is as described above.

Herein, the term "trans-polyisoprenoid" is a collective term for polymers containing tram-linked isoprene units $(C_5H_8)$ (in particular, the content of trans bonds is preferably at least 90%, more preferably at least 95%, still more preferably at least 97% of the total bonds). Examples of the trans-polyisoprenoid include trans-sesterterpenes $(C_{25})$, trans-triterpenes $(C_{30})$, trans-tetraterpenes $(C_{40})$, trans rubber such as trans-1,4-polyisoprene, and other polymers. Herein, the term "isoprenoid" refers to a compound containing an isoprene unit $(C_5H_8)$, and conceptually includes polyisoprenoids.

(Method for Producing Rubber Product)

The method for producing a rubber product of the first invention includes: kneading a trans-polyisoprenoid produced by the method for producing a trans-polyisoprenoid of the first invention with an additive to obtain a kneaded mixture; forming a raw rubber product from the kneaded mixture; and vulcanizing the raw rubber product.

The rubber product is not particularly limited as long as it is a rubber product that can be produced from rubber, preferably natural rubber, and examples include pneumatic tires, rubber rollers, rubber fenders, gloves, and medical rubber tubes.

In the case where the rubber product is a pneumatic tire; in other words, in the case where the method for producing a rubber product of the first invention is the method for producing a pneumatic tire of the first invention, the raw rubber product forming step corresponds to the step of building a green tire from the kneaded mixture, and the vulcanization step corresponds to the step of vulcanizing the green tire. Thus, the method for producing a pneumatic tire of the first invention includes: kneading a trans-polyisoprenoid produced by the method for producing a trans-polyisoprenoid with an additive to obtain a kneaded mixture; building a green tire from the kneaded mixture; and vulcanizing the green tire.

<Kneading Step>

In the kneading step, the trans-polyisoprenoid produced by the method for producing a trans-polyisoprenoid is kneaded with an additive to obtain a kneaded mixture.

The additive is not particularly limited, and additives used in production of rubber products may be used. For example, in the case where the rubber product is a pneumatic tire, examples of the additive include rubber components other than the trans-polyisoprenoid, reinforcing fillers such as carbon black, silica, calcium carbonate, alumina, clay, and talc, silane coupling agents, zinc oxide, stearic acid, processing aids, various antioxidants, softeners such as oils, waxes, vulcanizing agents such as sulfur, and vulcanization accelerators.

In the kneading step, a rubber kneading machine such as an open roll mill, a Banbury mixer, or an internal mixer may be used to perform kneading.

<Raw Rubber Product Forming Step (Green Tire Building Step in the Case of Tire))>

In the raw rubber product forming step, a raw rubber product (green tire in the case of tire) is formed from the kneaded mixture obtained in the kneading step.

The method for forming a raw rubber product is not particularly limited. Methods used to form raw rubber products may be used appropriately. For example, in the case where the rubber product is a pneumatic tire, the kneaded mixture obtained in the kneading step may be extruded according to the shape of a tire component and then formed in a usual manner on a tire building machine and assembled with other tire components to build a green tire (unvulcanized tire).

<Vulcanization Step>

In the vulcanization step, the raw rubber product obtained in the raw rubber product forming step is vulcanized to obtain a rubber product.

The method for vulcanizing the raw rubber product is not particularly limited. Methods used to vulcanize raw rubber products may be used appropriately. For example, in the case where the rubber product is a pneumatic tire, the green tire (unvulcanized tire) obtained in the raw rubber product forming step may be vulcanized by heating and pressing in a vulcanizer to obtain a pneumatic tire.

(Second Invention)
(Vector)

The vector of the second invention contains a nucleotide sequence in which a gene coding for a trans-prenyltransferase (tPT) family protein is functionally linked to a promoter having a promoter activity that drives laticifer-specific gene expression. By introducing such a vector into a plant for transformation, the gene coding for a protein involved in trans-polyisoprenoid biosynthesis in the vector can be expressed specifically in laticifers, thereby enhancing trans-isoprenoid or trans-polyisoprenoid production in the plant. This is probably because, if the expression of an exogenous gene introduced for the purpose of enhancing latex productivity is promoted in sites other than laticifers, a certain load is imposed on the metabolism or latex production of the plant, thereby causing adverse effects.

Herein, "promoter having a promoter activity that drives laticifer-specific gene expression" means that the promoter has activity to control gene expression to cause a desired gene to be expressed specifically in laticifers when the desired gene is functionally linked to the promoter and introduced into a plant. The term "laticifer-specific gene expression" means that the gene is expressed substantially exclusively in laticifers with no or little expression of the gene in sites other than laticifers in plants. Also, "a gene is functionally linked to a promoter" means that the gene sequence is linked downstream of the promoter so that the gene is controlled by the promoter.

The vector of the second invention can be prepared by inserting the nucleotide sequence of a promoter having a promoter activity that drives laticifer-specific gene expression and the nucleotide sequence of a gene coding for a trans-prenyltransferase (tPT) family protein into a vector commonly known as a plant transformation vector by conventional techniques. Examples of vectors that can be used to prepare the vector of the second invention include pBI vectors, binary vectors such as pGA482, pGAH, and pBIG, intermediate plasmids such as pLGV23Neo, pNCAT, and pMON200, and pH35GS containing GATEWAY cassette.

As long as the vector of the second invention contains the nucleotide sequence of a promoter having a promoter activity that drives laticifer-specific gene expression and the nucleotide sequence of a gene coding for a trans-prenyltransferase (tPT) family protein, it may contain additional nucleotide sequences. Usually, the vector contains vector-derived sequences in addition to these nucleotide sequences and further contains a restriction enzyme recognition sequence, a spacer sequence, a marker gene sequence, a reporter gene sequence, or other sequences.

Examples of the marker gene include drug-resistant genes such as kanamycin-resistant gene, hygromycin-resistant gene, and bleomycin-resistant gene. The reporter gene is intended to be introduced to determine the expression site in a plant, and examples include luciferase gene, β-glucuronidase (GUS) gene, green fluorescent protein (GFP), and red fluorescent protein (RFP).

The origin of the gene coding for a trans-prenyltransferase (tPT) family protein is not particularly limited. The gene may be derived from a microorganism, an animal, or a plant, preferably a plant, more preferably any of the plants mentioned above, still more preferably a rubber-producing plant, further preferably at least one selected from the group consisting of plants of the genera *Hevea*, *Sonchus*, *Taraxacum*, and *Parthenium*. In particular, it is especially preferably derived from at least one species of plant selected from the group consisting of *Hevea brasiliensis*, *Sonchus oleraceus*, *Parthenium argentatum*, and *Taraxacum kok-saghyz*, most preferably from *Hevea brasiliensis*.

The gene coding for a trans-prenyltransferase (tPT) family protein and the tPT family protein in the second invention are as described above concerning the first invention.

As long as the vector of the second invention contains the nucleotide sequence of a promoter having a promoter activity that drives laticifer-specific gene expression and the nucleotide sequence of a gene coding for a trans-prenyltransferase (tPT) family protein, it may further contain the nucleotide sequences of genes coding for additional proteins.

Examples of the genes coding for additional proteins include those described above concerning the first invention.

The promoter having a promoter activity that drives laticifer-specific gene expression is preferably at least one selected from the group consisting of a promoter of a gene coding for rubber elongation factor (REF), a promoter of a gene coding for small rubber particle protein (SRPP), a promoter of a gene coding for Hevein 2.1 (HEV2.1), and a promoter of a gene coding for MYC1 transcription factor (MYC1).

Herein, the term "rubber elongation factor (REF)" refers to a rubber particle-associated protein that is bound to rubber particles in the latex of rubber-producing plants such as *Hevea brasiliensis*, and contributes to stabilization of the rubber particles.

The term "small rubber particle protein (SRPP)" refers to a rubber particle-associated protein that is bound to rubber particles in the latex of rubber-producing plants such as *Hevea brasiliensis*.

The term "Hevein 2.1 (HEV2.1)" refers to a protein that is highly expressed in the laticifer cells of rubber-producing plants such as *Hevea brasiliensis*. This protein is involved in coagulation of rubber particles and has antifuingal activity.

The term "MYC1 transcription factor (MYC1)" refers to a transcription factor that is highly expressed in the latex of rubber-producing plants such as *Hevea brasiliensis* and participates in jasmonic acid signaling. The term "transcription factor" means a protein having activity to increase or decrease, preferably increase, gene transcription. In other words, MYC1 herein is a protein having activity (transcription factor activity) to increase or decrease, preferably increase, the transcription of a gene coding for at least one protein among the proteins involved in jasmonic acid signaling.

(Promoter of Gene Coding for Rubber Elongation Factor (REF))

The origin of the promoter of a gene coding for REF is not particularly limited, but the promotor is preferably derived from any of the plants mentioned above, more preferably a rubber-producing plant, still more preferably at least one selected from the group consisting of plants of the genera *Hevea, Sonchus, Taraxacum*, and *Parthenium*. In particular, it is further preferably derived from at least one species of plant selected from the group consisting of *Hevea brasiliensis, Sonchus oleraceus, Parthenium argentatum*, and *Taraxacum kok-saghyz*, particularly preferably from *Hevea brasiliensis*.

The promoter of a gene coding for REF is preferably any one of the following DNAs [A1] to [A3]:
[A1] a DNA having the nucleotide sequence represented by SEQ ID NO:10;
[A2] a DNA which hybridizes under stringent conditions to a DNA having a nucleotide sequence complementary to the nucleotide sequence represented by SEQ ID NO:10, and which has a promoter activity that drives laticifer-specific gene expression; and
[A3] a DNA which has a nucleotide sequence with at least 60% sequence identity to the nucleotide sequence represented by SEQ ID NO:10, and which has a promoter activity that drives laticifer-specific gene expression.

As used here, the term "hybridize" is as described above. Also, the stringent conditions are as described above.

Like the DNAs capable of hybridization under stringent conditions described above, it is known that promoters with nucleotide sequences having certain sequence identities to the original nucleotide sequence can also have promoter activity. In order to maintain the promoter activity, the sequence identity to the nucleotide sequence represented by SEQ ID NO:10 is at least 60%, preferably at least 80%, more preferably at least 90%, still more preferably at least 95%, further preferably at least 98%, particularly preferably at least 99%.

(Promoter of Gene Coding for SRPP)

The origin of the promoter of a gene coding for SRPP is not particularly limited, but the promoter is preferably derived from any of the plants mentioned above, more preferably a rubber-producing plant, still more preferably at least one selected from the group consisting of plants of the genera *Hevea, Sonchus, Taraxacum*, and *Parthenium*. In particular, it is further preferably derived from at least one species of plant selected from the group consisting of *Hevea brasiliensis, Sonchus oleraceus, Parthenium argentatum*, and *Taraxacum kok-saghyz*, particularly preferably from *Hevea brasiliensis*.

The promoter of a gene coding for SRPP is preferably any one of the following DNAs [B1] to [B3]:
[B1] a DNA having the nucleotide sequence represented by SEQ ID NO:11;
[B2] a DNA which hybridizes under stringent conditions to a DNA having a nucleotide sequence complementary to the nucleotide sequence represented by SEQ ID NO:11, and which has a promoter activity that drives laticifer-specific gene expression; and
[B3] a DNA which has a nucleotide sequence with at least 60% sequence identity to the nucleotide sequence represented by SEQ ID NO:11, and which has a promoter activity that drives laticifer-specific gene expression.

As used here, the term "hybridize" is as described above. Also, the stringent conditions are as described above.

Like the DNAs capable of hybridization under stringent conditions described above, it is known that promoters with nucleotide sequences having certain sequence identities to the original nucleotide sequence can also have promoter activity. In order to maintain the promoter activity, the sequence identity to the nucleotide sequence represented by SEQ ID NO:11 is at least 60%, preferably at least 80%, more preferably at least 90%, still more preferably at least 95%, further preferably at least 98%, particularly preferably at least 99%.

(Promoter of Gene Coding for HEV2.1)

The origin of the promoter of a gene coding for HEV2.1 is not particularly limited, but the promoter is preferably derived from any of the plants mentioned above, more preferably a rubber-producing plant, still more preferably at least one selected from the group consisting of plants of the genera *Hevea, Sonchus, Taraxacum*, and *Parthenium*. In particular, it is further preferably derived from at least one species of plant selected from the group consisting of *Hevea brasiliensis, Sonchus oleraceus, Parthenium argentatum*, and *Taraxacum kok-saghyz*, particularly preferably from *Hevea brasiliensis*.

The promoter of a gene coding for HEV2.1 is preferably any one of the following DNAs [C1] to [C3]:
[C1] a DNA having the nucleotide sequence represented by SEQ ID NO:12;
[C2] a DNA which hybridizes under stringent conditions to a DNA having a nucleotide sequence complementary to the nucleotide sequence represented by SEQ ID NO:12, and which has a promoter activity that drives laticifer-specific gene expression; and
[C3] a DNA which has a nucleotide sequence with at least 60% sequence identity to the nucleotide sequence represented by SEQ ID NO:12, and which has a promoter activity that drives laticifer-specific gene expression.

As used here, the term "hybridize" is as described above. Also, the stringent conditions are as described above.

Like the DNAs capable of hybridization under stringent conditions described above, it is known that promoters with nucleotide sequences having certain sequence identities to the original nucleotide sequence can also have promoter activity. In order to maintain the promoter activity, the sequence identity to the nucleotide sequence represented by SEQ ID NO:12 is at least 60%, preferably at least 80%, more preferably at least 90%, still more preferably at least 95%, further preferably at least 98%, particularly preferably at least 99%.

(Promoter of Gene Coding for MYC1)

The origin of the promoter of a gene coding for MYC1 is not particularly limited, but the promoter is preferably derived from any of the plants mentioned above, more preferably a rubber-producing plant, still more preferably at least one selected from the group consisting of plants of the genera *Hevea, Sonchus, Taraxacum*, and *Parthenium*. In particular, it is further preferably derived from at least one species of plant selected from the group consisting of *Hevea brasiliensis, Sonchus oleraceus, Parthenium argentatum*, and *Taraxacum kok-saghyz*, particularly preferably from *Hevea brasiliensis*.

The promoter of a gene coding for MYC1 is preferably any one of the following DNAs [D1] to [D3]:

[D1] a DNA having the nucleotide sequence represented by SEQ ID NO:13;

[D2] a DNA which hybridizes under stringent conditions to a DNA having a nucleotide sequence complementary to the nucleotide sequence represented by SEQ ID NO:13, and which has a promoter activity that drives laticifer-specific gene expression; and

[D3] a DNA which has a nucleotide sequence with at least 60% sequence identity to the nucleotide sequence represented by SEQ ID NO:13, and which has a promoter activity that drives laticifer-specific gene expression.

As used here, the term "hybridize" is as described above. Also, the stringent conditions are as described above.

Like the DNAs capable of hybridization under stringent conditions described above, it is known that promoters with nucleotide sequences having certain sequence identities to the original nucleotide sequence can also have promoter activity. In order to maintain the promoter activity, the sequence identity to the nucleotide sequence represented by SEQ ID NO:13 is at least 60%, preferably at least 80%, more preferably at least 90%, still more preferably at least 95%, further preferably at least 98%, particularly preferably at least 99%.

Whether the DNA which hybridizes to the above-mentioned DNA under stringent conditions or the DNA having at least 60% sequence identity to the above-mentioned DNA is a DNA having a promoter activity that drives laticifer-specific gene expression or not may be determined by conventional techniques, such as reporter assays using β-galactosidase, luciferase, green fluorescent protein (GFP), and other protein genes as reporter genes.

Conventional techniques may be employed to identify the nucleotide sequence of the promoter. For example, a genomic DNA is extracted from a growing plant by the cetyl trimethyl ammonium bromide (CTAB) method, then specific and random primers are designed based on the known nucleotide sequence of the promoter, and a gene including the promoter is amplified by TAIL (thermal asymmetric interlaced)-PCR using the extracted genomic DNA as a template to identify the nucleotide sequence.

The vector of the second invention (which contains a nucleotide sequence in which a gene coding for a trans-prenyltransferase (tPT) family protein is functionally linked to a promoter having a promoter activity that drives laticifer-specific gene expression) can be introduced into a plant to produce a transgenic plant transformed to express a certain protein involved in trans-polyisoprenoid biosynthesis specifically in laticifers. In the transgenic plant in which the certain protein involved in trans-polyisoprenoid biosynthesis is expressed specifically in the laticifers, a certain function, e.g., enzyme activity, of the protein newly expressed in the plant transfected with the vector of the second invention is enhanced in the laticifers to enhance a part of the trans-polyisoprenoid biosynthesis pathway. Therefore, trans-isoprenoid or trans-polyisoprenoid production can be enhanced in the plant.

The method for preparing the transgenic plant is explained briefly below, though such a transgenic plant can be prepared by conventional methods.

The plant into which the vector of the second invention is to be introduced to produce the transgenic plant is not particularly limited, but is preferably a rubber-producing plant, among others, because improved trans-polyisoprenoid productivity and increased trans-polyisoprenoid yield can be expected particularly when a tPT family protein is expressed in plants capable of biosynthesizing polyisoprenoids. In particular, it is further preferably derived from at least one species of rubber-producing plant selected from the group consisting of *Hevea brasiliensis, Sonchus oleraceus, Parthenium argentatum*, and *Taraxacum kok-saghyz*, particularly preferably from *Hevea brasiliensis*.

The vector of the second invention may be introduced into a plant (including plant cells, such as callus, cultured cells, spheroplasts, or protoplasts) by any method that can introduce DNA into plant cells. Examples include methods using *Agrobacterium* (JP S59-140885 A, JP S60-70080 A, WO94/00977), electroporation (JP S60-251887 A), and methods using particle guns (gene guns) (JP 2606856 B, JP 2517813 B). Among these, it is preferred to use a method using *Agrobacterium* (*Agrobacterium* method) to introduce the vector of the second invention into a plant to produce a transgenic plant (transgenic plant cells).

In addition, the vector of the second invention may also be introduced into, for example, an organism (e.g., a microorganism, yeast, animal cell, or insect cell) or a part thereof, an organ, a tissue, a cultured cell, a spheroplast, or a protoplast by any of the above-described DNA introduction methods to produce a trans-isoprenoid or trans-polyisoprenoid.

The transgenic plant (transgenic plant cells) can be produced by the above or other methods. The transgenic plant conceptually includes not only transgenic plant cells produced by the above methods, but also all of their progeny or clones and even progeny plants obtained by passaging the foregoing. Once obtaining transgenic plant cells into which the vector of the second invention has been introduced, progeny or clones can be produced from the transgenic plant cells by sexual or asexual reproduction, tissue culture, cell culture, cell fusion, or other techniques. Moreover, the transgenic plant cells, or their progeny or clones may be used to obtain reproductive materials (e.g., seeds, fruits, cuttings, stem tubers, root tubers, shoots, adventitious buds, adventitious embryos, callus, protoplasts), which can then be used to produce the transgenic plant on a large scale.

Techniques to regenerate plants (transgenic plants) from transgenic plant cells are already known; for example, Doi et al. disclose techniques for eucalyptus (JP 2000-316403 A), Fujimura et al. disclose techniques for rice (Fujimura et al., (1995), *Plant Tissue Culture Lett.*, vol. 2: p. 74-), Shillito et al. disclose techniques for corn (Shillito et al., (1989), *Bio/Technology*, vol. 7: p. 581-), Visser et al. disclose techniques for potato (Visser et al., (1989), *Theor. Appl. Genet.*, vol. 78: p. 589-), and Akama et al. disclose techniques for *Arabidopsis thaliana* (Akama et al., (1992), *Plant*

Cell Rep., vol. 12: p. 7-). A person skilled in the art can regenerate plants from the transgenic plant cells with reference to these documents.

Whether a target protein gene is expressed in regenerated plants or not may be determined by well-known methods. For example, Western blot analysis may be used to assess the expression of a target protein.

Seeds can be obtained from the transgenic plant, for example, as follows: the transgenic plant is rooted in an appropriate medium, transplanted to water-containing soil in a pot, and grown under proper cultivation conditions to finally produce seeds, which are then collected. Furthermore, plants can be grown from seeds, for example, as follows: seeds obtained from the transgenic plant as described above are sown in water-containing soil and grown under proper cultivation conditions into plants.

According to the second invention, by introducing the vector of the second invention into a plant, the gene coding for a protein involved in trans-polyisoprenoid biosynthesis (particularly preferably the gene coding for a tPT family protein) in the vector can be expressed specifically in laticifers, thereby enhancing trans-isoprenoid or trans-polyisoprenoid production in the plant. Specifically, a trans-isoprenoid or trans-polyisoprenoid may be produced by culturing, for example, transgenic plant cells produced as described above, callus obtained from the transgenic plant cells, or cells redifferentiated from the callus in an appropriate medium, or by growing, for example, transgenic plants regenerated from the transgenic plant cells, or plants grown from seeds obtained from these transgenic plants under proper cultivation conditions.

Thus, another aspect of the second invention relates to a method for enhancing trans-isoprenoid production in a plant by introducing the vector of the second invention into the plant. Furthermore, another aspect of the second invention relates to a method for enhancing trans-polyisoprenoid production in a plant by introducing the vector of the second invention into the plant.

(Method for Producing Rubber Product)

The method for producing a rubber product of the second invention includes: kneading a trans-polyisoprenoid produced by a transgenic plant with an additive to obtain a kneaded mixture, the transgenic plant being produced by introducing the vector of the second invention into a plant; forming a raw rubber product from the kneaded mixture; and vulcanizing the raw rubber product.

The rubber product is as described above concerning the first invention.

In the case where the rubber product is a pneumatic tire; in other words, in the case where the method for producing a rubber product of the second invention is the method for producing a pneumatic tire of the second invention, the raw rubber product forming step corresponds to the step of building a green tire from the kneaded mixture, and the vulcanization step corresponds to the step of vulcanizing the green tire. Thus, the method for producing a pneumatic tire of the second invention includes: kneading a trans-polyisoprenoid produced by a transgenic plant with an additive to obtain a kneaded mixture, the transgenic plant being produced by introducing the vector of the second invention into a plant; building a green tire from the kneaded mixture; and vulcanizing the green tire.

<Kneading Step>

In the kneading step, a trans-polyisoprenoid produced by a transgenic plant produced by introducing the vector of the second invention into a plant is kneaded with an additive to obtain a kneaded mixture.

The trans-polyisoprenoid produced by a transgenic plant produced by introducing the vector of the second invention into a plant can be obtained by harvesting latex from the transgenic plant, and subjecting the latex to the solidification step described below.

The method for harvesting latex from the transgenic plant is not particularly limited, and ordinary harvesting methods may be used. For example, latex may be harvested by collecting the emulsion oozing out from the cuts in the trunk of the plant (tapping), or the emulsion oozing out from the cut roots or other parts of the transgenic plant, or by crushing the cut tissue followed by extraction with an organic solvent.

<Solidification Step>

The harvested latex is subjected to a solidification step. The method for solidification is not particularly limited, and examples include a method of adding the latex to a solvent that does not dissolve the trans-polyisoprenoid (trans rubber), such as ethanol, methanol, or acetone; and a method of adding an acid to the latex. Rubber can be recovered as solids from the latex by the solidification step. The obtained rubber may be dried if necessary before use.

The additive is not particularly limited, and additives used in production of rubber products may be used. For example, in the case where the rubber product is a pneumatic tire, examples of the additive include rubber components other than the rubber obtained from the latex, reinforcing fillers such as carbon black, silica, calcium carbonate, alumina, clay, and talc, silane coupling agents, zinc oxide, stearic acid, processing aids, various antioxidants, softeners such as oils, waxes, vulcanizing agents such as sulfur, and vulcanization accelerators.

In the kneading step, a rubber kneading machine such as an open roll mill, a Banbury mixer, or an internal mixer may be used to perform kneading.

<Raw Rubber Product Forming Step (Green Tire Building Step in the Case of Tire)>

The raw rubber product forming step is as described above concerning the first invention.

<Vulcanization Step>

The vulcanization step is as described above concerning the first invention.

EXAMPLES

The present invention is specifically explained with reference to examples, but the present invention is not limited to these examples.

Example 1

[Extraction of Total RNA from *Hevea* Latex]

Total RNA was extracted from the latex of *Hevea brasiliensis* by the hot phenol method. To 6 mL of the latex were added 6 mL of 100 mM sodium acetate buffer and 1 mL of a 10% SDS solution, and then 12 mL of water-saturated phenol pre-heated at 65° C. The mixture was incubated for five minutes at 65° C., agitated in a vortex mixer, and centrifuged at 7000 rpm for 10 minutes at room temperature. After the centrifugation, the supernatant was transferred to a new tube, 12 mL of a phenol:chloroform (1:1) solution was added, and they were agitated by shaking for two minutes. After the agitation, the resulting mixture was centrifuged again at 7000 rpm for 10 minutes at room temperature. Then, the supernatant was transferred to a new tube, 12 mL of a chloroform:isoamyl alcohol (24:1) solution was added, and they were agitated by shaking for two minutes. After the agitation, the resulting mixture was centrifuged again at 7000 rpm for 10 minutes at room temperature. Then, the supernatant was transferred to a new tube, 1.2 mL of a 3M sodium acetate solution and 13 mL of isopropanol were added, and they were agitated in a vortex mixer. The resulting mixture was incubated for 30 minutes at −20° C. to precipitate total RNA. The incubated mixture was centrifuged at 15000 rpm for 10 minutes at 4° C., and the supernatant was removed to collect a precipitate of total RNA. The collected total RNA was washed twice with 70% ethanol, and then dissolved in RNase-free water.

[Synthesis of cDNA from Total RNA]

cDNA was synthesized from the collected total RNA. The cDNA synthesis was carried out using a PrimeScript II 1st strand cDNA synthesis kit (Takara) in accordance with the manual.

[Acquisition of tPT Gene from cDNA]

The prepared 1st strand cDNA was used as a template to obtain a tPT gene. PCR was performed using a KOD-plus-Neo (Toyobo Co., Ltd.) in accordance with the manual. The PCR reaction involved 35 cycles with each cycle consisting of 10 seconds at 98° C., 30 seconds at 58° C., and 1 minute at 68° C.

The tPT gene was obtained using the following primers.

```
Primer 1:
5'-ctgtattttcagggcggatatgtttcttcgaccaaggcc-3'

Primer 2:
5'-caaaactagtgcggccgcgctaatcaatccgttcgagattg-3'
```

A tPT gene (HbSDS) was prepared as described above. The sequence of the gene was isolated to identify the full-length nucleotide sequence. The nucleotide sequence of HbSDS is given by SEQ ID NO:1. The amino acid sequence of HbSDS estimated from the nucleotide sequence is also given by SEQ ID NO:2.

[Vector Construction]

The obtained DNA fragment was subjected to dA addition and then inserted into a pGEM-T Easy vector using a pGEM-T Easy Vector System (Promega) to prepare pGEM-HbSDS.

[Transformation of *Escherichia coli*]

*Escherichia coli* DH5a was transformed with the prepared vector, the transformant was cultured on LB agar medium containing ampicillin and X-gal, and *Escherichia coli* cells carrying the introduced target gene were selected by blue/white screening.

[Plasmid Extraction]

The *Escherichia coli* cells transformed with the plasmid containing the target gene were cultured overnight at 37° C. on LB liquid medium. After the culture, the cells were collected, and the plasmid was collected using a FastGene Plasmid mini kit (Nippon Genetics Co., Ltd.).

It was confirmed by sequence analysis that there were no mutations in the nucleotide sequence of the collected gene inserted in the plasmid.

[Preparation of Vector for Cell-Free Protein Synthesis]

The pGEM-HbSDS acquired in the above [Vector construction] was treated with the restriction enzyme BstZ I, and then a HbSDS fragment was collected. The fragment was mixed with a pEU-E01-His-TEV-MCS-N2 cell-free expression vector that had been treated with the restriction enzymes EcoR I and Kpn I, and they were connected by in vitro homologous recombination to prepare pEU-His-N2-HbSDS.

[Transformation of *Escherichia coli*]

*Escherichia coli* DH5α was transformed with the prepared vector, the transformant was cultured on LB agar medium containing ampicillin and X-gal, and *Escherichia coli* cells carrying the introduced target gene were screened by colony PCR.

[Plasmid Extraction]

The *Escherichia coli* cells transformed with the plasmid containing the target gene were cultured overnight at 37° C. on LB liquid medium. After the culture, the cells were collected, and the plasmid was collected using a FastGene Plasmid mini kit (Nippon Genetics Co., Ltd.).

[Preparation of Rubber Particles]

Rubber particles were prepared from *Hevea* latex by five stages of centrifugation. To 900 mL of *Hevea* latex was added 100 mL of 1 M Tris buffer (pH 7.5) containing 20 mM dithiothreitol (DT) to prepare a latex solution. The latex solution was centrifuged in stages at the following different speeds: 1000×g, 2000×g, 8000×g, 20000×g, and 50000×g. Each stage of centrifugation was carried out for 45 minutes at 4° C. To the rubber particle layer left after the centrifugation at 50000×g was added 3-[(3-cholamidopropyl)dimethylamino]-propanesulfonate (CHAPS) at a final concentration of 0.1 to 2.0×CMC (0.1 to 2.0 times the critical micelle concentration CMC) to wash the rubber particles. After the washing, the rubber particles were collected by ultracentrifugation (40000×g, 4° C., 45 minutes) and re-suspended in an equal amount of 100 M Tris buffer (pH 7.5) containing 2 mM dithiothreitol (DT).

[Cell-Free Protein Synthesis Reaction (Step 1: mRNA Transcription Reaction)]

Cell-free protein synthesis was performed using a WEPRO7240H expression kit (CellFree Sciences Co., Ltd.). An mRNA transcription reaction was performed using the vector acquired in the above [Preparation of vector for cell-free protein synthesis] as a template in accordance with the protocol of the WEPRO7240H expression kit.

[Purification of mRNA]

After the transcription reaction, the resulting mRNA was purified by ethanol precipitation.

[Cell-Free Protein Synthesis Reaction (Step 2: Protein Synthesis by Dialysis)]

The following amounts of materials were added to a dialysis cup (MWCO 12000, Bio-Teck). A total amount of 60 μL of a reaction solution was prepared according to the protocol of the WEPRO7240H expression kit. To the reaction solution was added 1 to 2 mg of the rubber particles. Separately, 650 μL of SUB-AMIX was added to a No. 2 PP container (Maruemu container).

Figure 3:
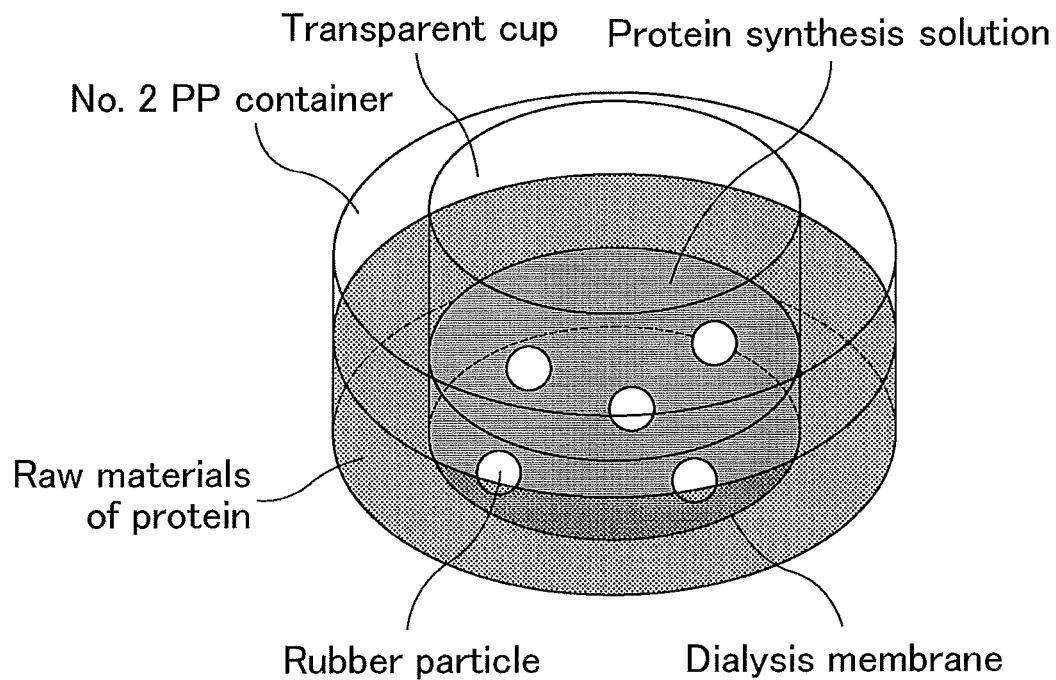
FIG. 3 is an outline diagram illustrating the dialysis process in Example.

The dialysis cup was set in the No. 2 PP container, and a protein synthesis reaction was initiated at 26° C. The addition of the mRNA and the replacement of the external dialysis solution (SUB-AMIX) were performed twice after the initiation of the reaction. The reaction was carried out for 24 hours. FIG. 3 shows an outline diagram illustrating the dialysis process.

[Collection of Reacted Rubber Particles]

The solution in the dialysis cup was transferred to a new 1.5 μL tube, and the reacted rubber particles were collected by ultracentrifugation (40000×g, 4° C., 45 minutes) and re-suspended in an equal amount of 100 M Tris buffer (pH 7.5) containing 2 mM dithiothreitol (DTT).

[Measurement of Rubber Synthesis Activity of Reacted Rubber Particles]

The rubber synthesis activity of the collected reacted rubber particles was measured as follows.

First, 50 mM Tris-HCl (pH 7.5), 2 mM DTT, 5 mM $MgCl_2$, 15 μM farnesyl diphosphate (FPP), 100 μM 1-14C isopentenyl diphosphate ([1-14C]IPP, specific activity 5 Ci/mol), and 10 µL of the rubber particle solution were mixed to prepare a reaction solution (100 µL in total), which was then reacted for 16 hours at 30° C.

After the reaction, 200 µL of saturated NaCl was added to the solution, and isopentenol and the like were extracted from the mixture with 1 mL of diethyl ether. Next, polyprenyl diphosphates were extracted from the aqueous phase with 1 mL of BuOH saturated with saline, and then a very long chain polyisoprenoid (trans-1,4-polyisoprene) was further extracted from the aqueous phase with 1 mL of toluene/hexane (1:1), followed by determination of radioactivity. The radioactivity of each phase was determined by $^{14}$C counting using a liquid scintillation counter. A higher radioactivity (dpm) indicates higher production of very long chain polyisoprenoid (trans-1,4-polyisoprene) and higher rubber synthesis activity.

Table 1 shows the results. The "Rubber synthesis activity difference (dpm)" in Table 1 represents the difference from the radioactivity of Comparative Example 1 in which the rubber particles were bound to nothing as described later.

[Measurement of Molecular Weight Distribution of Synthesized Very Long Chain Polyisoprenoid]

Figure 4:
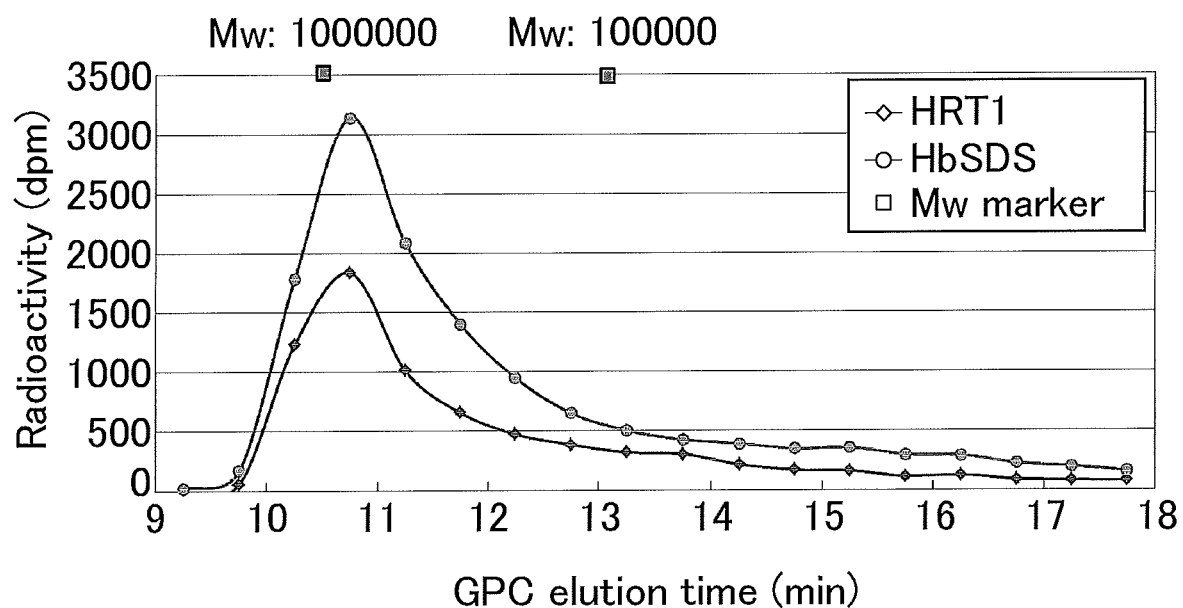
FIG. 4 illustrates a graph of the measured molecular weight distributions of the very long chain polyisoprenoids synthesized in Example 1 and Comparative Example 2.

The molecular weight distribution of the very long chain polyisoprenoid (trans-1,4-polyisoprene) synthesized as described above was measured under the following conditions by radio-HPLC. FIG. 4 shows the results.
HPLC system: a product of GILSON
Column: TSK guard column MP(XL) available from Tosoh Corporation, TSK gel Multipore HXL-M (two columns)
Column temperature: 40° C.
Solvent: THF available from Merck
Flow rate: 1 mL/min
UV detection: 215 nm
RI detection: Ramona Star (Raytest GmbH)

Comparative Example 1

[Preparation of Rubber Particles]
The same procedure as in Example 1 was followed.
[Cell-Free Protein Synthesis Reaction (Step 1: mRNA Transcription Reaction)]
Cell-free protein synthesis was performed using a WEPRO7240H expression kit (CellFree Sciences Co., Ltd.). An mRNA transcription reaction was performed using the cell-free expression vector pEU-E01-His-TEV-MCS-N2 as a template in accordance with the protocol of the WEPRO7240H expression kit.
[Purification of mRNA]
After the transcription reaction, the resulting mRNA was purified by ethanol precipitation.
[Cell-Free Protein Synthesis Reaction (Step 2: Protein Synthesis by Dialysis)]
The same procedure as in Example 1 was followed but using the prepared mRNA.
[Collection of Reacted Rubber Particles]
The reacted rubber particles were collected as in Example 1 and re-suspended in an equal amount of 100 M Tris buffer (pH 7.5) containing 2 mM dithiothreitol (DT).
[Measurement of Rubber Synthesis Activity of Reacted Rubber Particles]
The rubber synthesis activity of the collected reacted rubber particles was measured as in Example 1.
Table 1 shows the results.

Comparative Example 2

[Acquisition of CPT Gene from cDNA]
The 1st strand cDNA prepared in [Synthesis of cDNA from total RNA] in Example 1 was used as a template to obtain a CPT gene. PCR was performed using a KOD-plus-Neo (Toyobo Co., Ltd.) in accordance with the manual. The PCR reaction involved 35 cycles with each cycle consisting of 10 seconds at 98° C., 30 seconds at 58° C., and 1 minute at 68° C.

The CPT gene was obtained using the following primers.

```
Primer 3:
5'-tttggatccgatggaattatacaacggtgagagg-3'

Primer 4:
5'-tttgcggccgcttattttaagtattccttatgtttctcc-3'
```

A CPT gene (HRT1) was prepared as described above. The gene was sequenced to identify the full-length nucleotide sequence and amino acid sequence. The nucleotide sequence of HRT1 is given by SEQ ID NO:18. The amino acid sequence of HRT1 is given by SEQ ID NO:19.
[Vector Construction]
The obtained DNA fragment was subjected to dA addition and then inserted into a pGEM-T Easy vector using a pGEM-T Easy Vector System (Promega) to prepare pGEM-HRT1.
[Transformation of *Escherichia coli*]
The same procedure as in Example 1 was followed but using the prepared vector.
[Plasmid Extraction]
The same procedure as in Example 1 was followed.
[Preparation of Vector for Cell-Free Protein Synthesis]
The pGEM-HRT1 acquired in the above [Vector construction] was treated with the restriction enzymes Bam HI and Not I, and inserted into a pEU-E01-His-TEV-MCS-N2 cell-free expression vector that had been treated similarly with the restriction enzymes Bam HI and Not I to prepare pEU-His-N2-HRT1.
[Transformation of *Escherchia coli*]
The same procedure as in Example 1 was followed but using the prepared vector.
[Plasmid Extraction]
The same procedure as in Example 1 was followed.
[Preparation of Rubber Particles]
The same procedure as in Example 1 was followed.
[Cell-Free Protein Synthesis Reaction (Step 1: mRNA Transcription Reaction)]
Cell-free protein synthesis was performed using a WEPRO7240H expression kit (CellFree Sciences Co., Ltd.). An mRNA transcription reaction was performed using the vector pEU-His-N2-HRT1 acquired in the above [Preparation of vector for cell-free protein synthesis] as a template in accordance with the protocol of the WEPRO7240H expression kit.
[Purification of mRNA]
After the transcription reaction, the resulting mRNA was purified by ethanol precipitation.
[Cell-Free Protein Synthesis Reaction (Step 2: Protein Synthesis by Dialysis)]
The same procedure as in Example 1 was followed but using the prepared mRNA.
[Collection of Reacted Rubber Particles]
The reacted rubber particles were collected as in Example 1 and re-suspended in an equal amount of 100 M Tris buffer (pH 7.5) containing 2 mM dithiothreitol (DTT).

[Measurement of Rubber Synthesis Activity of Reacted Rubber Particles]

The rubber synthesis activity of the collected reacted rubber particles was measured as in Example 1.

Table 1 shows the results.

[Measurement of Molecular Weight Distribution of Synthesized Very Long Chain Polyisoprenoid]

The molecular weight distribution of the very long chain polyisoprenoid synthesized in the above [Measurement of rubber synthesis activity of reacted rubber particles] was measured as in Example 1. FIG. 4 shows the results.

TABLE 1

|  | Bound protein | Rubber synthesis activity difference (dpm) |
|---|---|---|
| Comparative Example 1 | None | — |
| Comparative Example 2 | HRT1 | 83700 |
| Example 1 | HbSDS | 93000 |

Table 1 demonstrate that a very long chain polyisoprenoid was synthesized when rubber particles were bound to a tPT family protein (Example 1), similarly to when rubber particles were bound to HRT1, a cis-prenyltransferase family protein (Comparative Example 2). This is in contrast to when rubber particles were bound to nothing (Comparative Example 1).

As shown in FIG. 4, the very long chain polyisoprenoid synthesized in Example 1 is a long chain rubber that showed the highest peak at a GPC elution time corresponding to a weight average molecular weight of about 1,000,000. It is also considered that the very long chain polyisoprenoid synthesized in Example 1 had a molecular weight distribution pattern comparable to that of the very long chain polyisoprenoid synthesized in Comparative Example 2. It should be noted that in FIG. 4, peak heights cannot be used to compare activities because the results were not standardized among the samples.

<In Silico Estimation of Conserved Regions of tPT Family Proteins>

Multiple sequence alignment of the tPT family proteins derived from various organisms shown in FIG. 5 was performed to search highly conserved sequence parts (conserved regions). FIG. 5 shows the alignment results around the conserved regions.

The multiple sequence alignment was carried out using software called Genetyx Ver. 11.

In FIG. 5, Erg20p (Yeast TPT (FPPS)) corresponds to a sequence of positions 91 to 150 or positions 227 to 285 of FPPS from yeast represented by SEQ ID NO:3;

EuFPPS (*Eucommia ulmoides* TPT) corresponds to a sequence of positions 90 to 149 or positions 225 to 283 of EuFPPS from *Eucommia ulmoides* represented by SEQ ID NO:4;

HbFPPS (HeveaTPT) corresponds to a sequence of positions 84 to 143 or positions 219 to 277 of HbFPPS from *Hevea brasiliensis* represented by SEQ ID NO:5;

Coq1p (Yeast TPT) corresponds to a sequence of positions 82 to 135 or positions 249 to 307 of TPT from yeast represented by SEQ ID NO:6;

AtSDS1 (ArabiTPT) corresponds to a sequence of positions 162 to 215 or positions 285 to 343 of AtSDS1 from *Arabidopsis thaliana* represented by SEQ ID NO:7;

HbSDS (HeveaTPT) corresponds to a sequence of positions 174 to 227 or positions 297 to 355 of HbSDS from *Hevea brasiliensis* represented by SEQ ID NO:2;

HsTPT (HumanTPT) corresponds to a sequence of positions 132 to 185 or positions 255 to 313 of HsTPT from human represented by SEQ ID NO:8; and MmTPT (MouseTPT) corresponds to a sequence of positions 92 to 145 or positions 215 to 273 of MmTPT from mouse represented by SEQ ID NO:9.

According to literature, such as Andrew H.-J. Wang et al., Eur. J. Biochem. 269, pp. 3339-3354 (2002), box A (corresponding to positions 183 to 187 of HbSDS from *Hevea brasiliensis* represented by SEQ ID NO:2) and box B (corresponding to positions 310 to 314 of HbSDS from *Hevea brasiliensis* represented by SEQ ID NO:2) in FIG. 5 are parts of highly conserved regions of tPT family proteins derived from various organisms. In particular, it is considered that an amino acid sequence at positions corresponding to positions 183 to 187 of HbSDS from *Hevea brasiliensis* represented by SEQ ID NO:2, and an amino acid sequence at positions corresponding to positions 310 to 314 of HbSDS from *Hevea brasiliensis* represented by SEQ ID NO:2 are conserved as specific motifs (amino acid sequences (A1) or (A2) and (B)), and proteins having these motifs at the respective positions have the functions of tPT family proteins.

The following is understood from FIG. 5.

The conserved region in box A corresponding to positions 183 to 187 of HbSDS from *Hevea brasiliensis* represented by SEQ ID NO:2 corresponds to:

positions 100 to 104 of FPPS from yeast represented by SEQ ID NO:3;

positions 99 to 103 of EuFPPS from *Eucommia ulmoides* represented by SEQ ID NO:4;

positions 93 to 97 of HbFPPS from *Hevea brasiliensis* represented by SEQ ID NO:5;

positions 91 to 95 of TPT from yeast represented by SEQ ID NO:6;

positions 171 to 175 of AtSDS1 from *Arabidopsis thaliana* represented by SEQ ID NO:7;

positions 141 to 145 of HsTPT from human represented by SEQ ID NO:8; or positions 101 to 105 of MmTPT from mouse represented by SEQ ID NO:9.

The conserved region in box B corresponding to positions 310 to 314 of HbSDS from *Hevea brasiliensis* represented by SEQ ID NO:2 corresponds to:

positions 240 to 244 of FPPS from yeast represented by SEQ ID NO:3;

positions 238 to 242 of EuFPPS from *Eucommia ulmoides* represented by SEQ ID NO:4;

positions 232 to 236 of HbFPPS from *Hevea brasiliensis* represented by SEQ ID NO:5;

positions 262 to 266 of TPT from yeast represented by SEQ ID NO:6;

positions 298 to 302 of AtSDS1 from *Arabidopsis thaliana* represented by SEQ ID NO:7;

positions 268 to 272 of HsTPT from human represented by SEQ ID NO:8; or positions 228 to 232 of MmTPT from mouse represented by SEQ ID NO:9.

(Sequence Listing Free Text)

SEQ ID NO:1: Nucleotide sequence of gene coding for HbSDS from *Hevea brasiliensis*

SEQ ID NO:2: Amino acid sequence of HbSDS from *Hevea brasiliensis*

SEQ ID NO:3: Amino acid sequence of FPPS from yeast

SEQ ID NO:4: Amino acid sequence of EuFPPS from *Eucommia ulmoides*
SEQ ID NO:5: Amino acid sequence of HbFPPS from *Hevea brasiliensis*
SEQ ID NO:6: Amino acid sequence of TPT from yeast
SEQ ID NO:7: Amino acid sequence of AtSDS1 from *Arabidopsis thaliana*
SEQ ID NO:8: Amino acid sequence of HsTPT from human
SEQ ID NO:9: Amino acid sequence of MmTPT from mouse
SEQ ID NO:10: Nucleotide sequence of promoter of gene coding for rubber elongation factor from *Hevea brasiliensis*
SEQ ID NO:11: Nucleotide sequence of promoter of gene coding for small rubber particle protein from *Hevea brasiliensis*
SEQ ID NO:12: Nucleotide sequence of promoter of gene coding for Hevien 2.1 from *Hevea brasiliensis*
SEQ ID NO:13: Nucleotide sequence of promoter of gene coding for MYC1 transcription factor from *Hevea brasiliensis*
SEQ ID NO:14: Primer 1
SEQ ID NO:15: Primer 2
SEQ ID NO:16: Primer 3
SEQ ID NO:17: Primer 4
SEQ ID NO:18: Nucleotide sequence of gene coding for HRT1 from *Hevea brasiliensis*
SEQ ID NO:19: Amino acid sequence of HRT1 from *Hevea brasiliensis*

The invention claimed is:

1. A method for producing a trans-polyisoprenoid, the method comprising:
   binding a protein expressed from a gene coding for a trans-prenyltransferase (tPT) family protein to rubber particles in vitro,
   wherein said binding is that said protein is fully or partially incorporated into the rubber particle, or the protein is inserted into a membrane structure of the rubber particle, and
   wherein the binding comprises performing protein synthesis in the presence of both rubber particles and a cell-free protein synthesis solution containing an mRNA coding for a trans-prenyltransferase (tPT) family protein to bind the tPT family protein to the rubber particles.

2. The method for producing a trans-polyisoprenoid according to claim 1,
   wherein the gene coding for a trans-prenyltransferase (tPT) family protein is derived from a plant.

3. The method for producing a trans-polyisoprenoid according to claim 2,
   wherein the gene coding for a trans-prenyltransferase (tPT) family protein is derived from a rubber-producing plant.

4. The method for producing a trans-polyisoprenoid according to claim 3,
   wherein the gene coding for a trans-prenyltransferase (tPT) family protein is derived from Hevea brasiliensis.

5. The method for producing a trans-polyisoprenoid according to claim 1,
   wherein the cell-free protein synthesis solution comprises a germ extract.

6. The method for producing a trans-polyisoprenoid according to claim 5,
   wherein the germ extract is derived from wheat.

7. The method for producing a trans-polyisoprenoid according to claim 1,
   wherein the rubber particles are present in the cell-free protein synthesis solution at a concentration of 5 to 50 g/L.

* * * * *

```
                            SEQUENCE LISTING

<160> NUMBER OF SEQ ID NOS: 19

<210> SEQ ID NO 1
<211> LENGTH: 1257
<212> TYPE: DNA
<213> ORGANISM: Hevea brasiliensis

<400> SEQUENCE: 1
atgatgtcaa tgacatgcta cagtcttgat tttggaagga ctgtgtttga tttggcggct     60
tgtgggtgct cctccaatgc ttcaatagat aggtgttcag tgaggaatta tgcaaggtcg    120
gtttatagga cttgtaatag agactatgct gctagaagat cgccctattg ccggcgagat    180
agtgcttggt gtcgagtttc ttcgaccaag gcccctgaga ctttacttaa cggggttagt    240
caagatcctg ctgtaaattt gaaggagtca agaggcccaa tttcattgat aaatgtgttt    300
gaagcggttg ctggtgatct ccagactctc aaccaaaacc tccggtcgat tgttggtgca    360
gaaaacccag ttttaatgtc tgcagctgat cagatatttg gtgctggtgg aaaaggatg    420 cgaccagctt tggtattcct agtgtcaaga gccacagcag aaatagtagg gttaaaagaa    480
ctcactacga aacatcgacg tttagcagag atcattgaga tgatccatac tgcaagctta    540
attcatgatg atgtactaga tgaaagtaac atgcgaagag gaaacaaac ggttcatcaa     600 ctgtatggca cgagggtggc agtactggct ggggatttca tgtttgctca gtcctcatgg    660
tacctagcaa atcttgaaaa cattgaagtc attaagctta tcagccaggt tattaaagat    720
tttgcaagtg gtgaaataaa gcaagcatct agtttgtttg actgcgatgt tgaactcgag    780
gagtacttga tcaagagcta ttacaaaact gcctctttaa ttgctgcaag taccaaagga    840
gctgctattt ttagtgggt ggacagcagt gttgctgaac aaatgtatga atatggtaag     900
aatcttggtc tgtccttcca agttgttgac gacgtactgg attttacgca gtcagcagag    960
cagctgggga agccagctgg cagtgacttg gcaaaaggga accttaccgc ccctgtaata   1020
tttgctctgg agaaagaacc aaaactgaga gaaatcattg agtctgaatt ctgtgagact   1080
ggttctctgg atgaagctgt tgagttggtt aagcagtgtg ggggtattga aagagcacaa   1140
gaattagcga aggagaaagc tgatcttgca atacagaatc ttaattgtct tcctcggggt   1200
gtatttcaat cacatctcaa agaaatggtg ttgtacaatc tcgaacggat tgattag      1257

<210> SEQ ID NO 2
<211> LENGTH: 418
<212> TYPE: PRT
<213> ORGANISM: Hevea brasiliensis

<400> SEQUENCE: 2
```

```
Met Met Ser Met Thr Cys Tyr Ser Leu Asp Phe Gly Arg Thr Val Phe
1               5                   10                  15

Asp Leu Ala Ala Cys Gly Cys Ser Ser Asn Ala Ser Ile Asp Arg Cys
            20                  25                  30

Ser Val Arg Asn Tyr Ala Arg Ser Val Tyr Arg Thr Cys Asn Arg Asp
        35                  40                  45

Tyr Ala Ala Arg Arg Ser Pro Tyr Cys Arg Arg Asp Ser Ala Trp Cys
    50                  55                  60

Arg Val Ser Ser Thr Lys Ala Pro Glu Thr Leu Leu Asn Gly Val Ser
65                  70                  75                  80

Gln Asp Pro Ala Val Asn Leu Lys Glu Ser Arg Gly Pro Ile Ser Leu
                85                  90                  95

Ile Asn Val Phe Glu Ala Val Ala Gly Asp Leu Gln Thr Leu Asn Gln
            100                 105                 110

Asn Leu Arg Ser Ile Val Gly Ala Glu Asn Pro Val Leu Met Ser Ala
        115                 120                 125

Ala Asp Gln Ile Phe Gly Ala Gly Gly Lys Arg Met Arg Pro Ala Leu
    130                 135                 140

Val Phe Leu Val Ser Arg Ala Thr Ala Glu Ile Val Gly Leu Lys Glu
145                 150                 155                 160

Leu Thr Thr Lys His Arg Arg Leu Ala Glu Ile Ile Glu Met Ile His
                165                 170                 175

Thr Ala Ser Leu Ile His Asp Asp Val Leu Asp Glu Ser Asn Met Arg
            180                 185                 190

Arg Gly Lys Gln Thr Val His Gln Leu Tyr Gly Thr Arg Val Ala Val
        195                 200                 205

Leu Ala Gly Asp Phe Met Phe Ala Gln Ser Ser Trp Tyr Leu Ala Asn
    210                 215                 220

Leu Glu Asn Ile Glu Val Ile Lys Leu Ile Ser Gln Val Ile Lys Asp
225                 230                 235                 240

Phe Ala Ser Gly Glu Ile Lys Gln Ala Ser Ser Leu Phe Asp Cys Asp
                245                 250                 255

Val Glu Leu Glu Glu Tyr Leu Ile Lys Ser Tyr Lys Thr Ala Ser
            260                 265                 270

Leu Ile Ala Ala Ser Thr Lys Gly Ala Ala Ile Phe Ser Gly Val Asp
        275                 280                 285

Ser Ser Val Ala Glu Gln Met Tyr Glu Tyr Gly Lys Asn Leu Gly Leu
    290                 295                 300

Ser Phe Gln Val Val Asp Asp Val Leu Asp Phe Thr Gln Ser Ala Glu
305                 310                 315                 320

Gln Leu Gly Lys Pro Ala Gly Ser Asp Leu Ala Lys Gly Asn Leu Thr
                325                 330                 335

Ala Pro Val Ile Phe Ala Leu Glu Lys Glu Pro Lys Leu Arg Glu Ile
            340                 345                 350

Ile Glu Ser Glu Phe Cys Glu Thr Gly Ser Leu Asp Glu Ala Val Glu
        355                 360                 365

Leu Val Lys Gln Cys Gly Gly Ile Glu Arg Ala Gln Glu Leu Ala Lys
    370                 375                 380

Glu Lys Ala Asp Leu Ala Ile Gln Asn Leu Asn Cys Leu Pro Arg Gly
385                 390                 395                 400

Val Phe Gln Ser His Leu Lys Glu Met Val Leu Tyr Asn Leu Glu Arg
                405                 410                 415
```

Ile Asp

<210> SEQ ID NO 3
<211> LENGTH: 352
<212> TYPE: PRT
<213> ORGANISM: Saccharomyces cerevisiae

<400> SEQUENCE: 3

```
Met Ala Ser Glu Lys Glu Ile Arg Arg Glu Arg Phe Leu Asn Val Phe
1               5                   10                  15

Pro Lys Leu Val Glu Glu Leu Asn Ala Ser Leu Leu Ala Tyr Gly Met
                20                  25                  30

Pro Lys Glu Ala Arg Asp Trp Tyr Ala His Ser Leu Asn Tyr Asn Thr
            35                  40                  45

Pro Gly Gly Lys Leu Asn Arg Gly Leu Ser Val Asp Thr Tyr Ala
        50                  55                  60

Ile Leu Ser Asn Lys Thr Val Glu Gln Leu Gly Gln Glu Glu Tyr Glu
65                  70                  75                  80

Lys Val Ala Ile Leu Gly Trp Cys Ile Glu Leu Leu Gln Ala Tyr Phe
                85                  90                  95

Leu Val Ala Asp Asp Met Met Asp Lys Ser Ile Thr Arg Arg Gly Gln
                100                 105                 110

Leu Cys Trp Tyr Lys Val Pro Glu Val Gly Glu Ile Ala Ile Asn Asp
            115                 120                 125

Ala Phe Met Leu Glu Ala Ala Ile Tyr Lys Leu Leu Lys Ser His Phe
        130                 135                 140

Arg Asn Glu Lys Tyr Tyr Ile Asp Ile Thr Glu Leu Phe His Glu Val
145                 150                 155                 160

Thr Phe Gln Thr Glu Leu Gly Gln Leu Met Asp Leu Ile Thr Ala Pro
                165                 170                 175

Glu Asp Lys Val Asp Leu Ser Lys Phe Ser Leu Lys Lys His Ser Phe
                180                 185                 190

Ile Val Thr Phe Lys Thr Ala Tyr Tyr Ser Phe Tyr Leu Pro Val Ala
            195                 200                 205

Leu Ala Met Tyr Val Ala Gly Ile Thr Asp Glu Lys Asp Leu Lys Gln
        210                 215                 220

Ala Arg Asp Val Leu Ile Pro Leu Gly Glu Tyr Phe Gln Ile Gln Asp
225                 230                 235                 240

Asp Tyr Leu Asp Cys Phe Gly Thr Pro Glu Gln Ile Gly Lys Ile Gly
                245                 250                 255

Thr Asp Ile Gln Asp Asn Lys Cys Ser Trp Val Ile Asn Lys Ala Leu
                260                 265                 270

Glu Leu Ala Ser Ala Glu Gln Arg Lys Thr Leu Asp Glu Asn Tyr Gly
            275                 280                 285

Lys Lys Asp Ser Val Ala Glu Ala Lys Cys Lys Lys Ile Phe Asn Asp
        290                 295                 300

Leu Lys Ile Glu Gln Leu Tyr His Glu Tyr Glu Ser Ile Ala Lys
305                 310                 315                 320

Asp Leu Lys Ala Lys Ile Ser Gln Val Asp Glu Ser Arg Gly Phe Lys
                325                 330                 335

Ala Asp Val Leu Thr Ala Phe Leu Asn Lys Val Tyr Lys Arg Ser Lys
                340                 345                 350
```

<210> SEQ ID NO 4
<211> LENGTH: 348

```
<212> TYPE: PRT
<213> ORGANISM: Eucommia ulmoides

<400> SEQUENCE: 4

Met Ala Glu Leu Lys Lys Glu Phe Leu Asn Val Tyr Ser Val Leu Lys
1               5                   10                  15

Lys Glu Leu Leu His Asp Pro Ala Phe Ser Leu Thr Glu Asp Ser Arg
            20                  25                  30

Asn Trp Val Glu Arg Met Leu Asp Tyr Asn Val Pro Gly Gly Lys Leu
        35                  40                  45

Asn Arg Gly Leu Ser Val Val Asp Ser Tyr Lys Leu Leu Lys Glu Leu
    50                  55                  60

Ser Ser Ser Lys Lys Gly Ala Gln Leu Thr Glu Ser Glu Ile Phe His
65                  70                  75                  80

Ser Ser Val Leu Gly Trp Cys Ile Glu Trp Leu Gln Ala Cys Ala Leu
                85                  90                  95

Val Leu Asp Asp Ile Met Asp Ser Ser His Thr Arg Arg Gly Gln Met
            100                 105                 110

Cys Trp Tyr Lys Leu Pro Lys Val Gly Met Ile Ala Ile Asn Asp Gly
        115                 120                 125

Leu Ile Leu Arg Asn His Val Pro Arg Ile Leu Lys Lys His Phe Arg
    130                 135                 140

Ser Lys Pro Tyr Tyr Leu Glu Leu Leu Asp Leu Phe His Glu Val Glu
145                 150                 155                 160

Cys Gln Thr Val Gly Gly Gln Met Ile Asp Leu Ile Thr Thr Leu Val
                165                 170                 175

Gly Glu Ile Asp Leu Ser Glu Tyr Ser Leu Pro Thr His Arg Gln Ile
            180                 185                 190

Thr Val Ser Lys Thr Ser Tyr Tyr Ser Phe Tyr Leu Pro Val Ala Cys
        195                 200                 205

Ala Leu Leu Met Thr Gly Glu Lys Leu Glu Ser His Ser Gly Met Lys
    210                 215                 220

Asp Ile Leu Ile Glu Met Gly Ser Tyr Phe Gln Val Gln Asp Asp Tyr
225                 230                 235                 240

Leu Asp Cys Phe Gly Asp Pro Glu Val Ile Gly Lys Ile Gly Ser Asp
                245                 250                 255

Ile Glu Asp Phe Lys Cys Thr Trp Leu Val Val Lys Ala Leu Glu Leu
            260                 265                 270

Cys Asn Glu Glu Gln Lys Lys Ile Leu Tyr Asp Asn Tyr Gly Lys Lys
        275                 280                 285

Asp Pro Glu Ser Val Ala Arg Val Lys Asp Leu Tyr Lys Thr Leu Lys
    290                 295                 300

Leu Gln Asp Val Phe Glu Glu Tyr Glu Lys Lys Thr His Glu Lys Leu
305                 310                 315                 320

Asn Lys Ser Ile Asp Ala Tyr Pro Ser Lys Ala Val Gln Ala Val Leu
                325                 330                 335

Gln Ser Phe Leu Ala Lys Ile His Arg Arg Leu Lys
            340                 345

<210> SEQ ID NO 5
<211> LENGTH: 342
<212> TYPE: PRT
<213> ORGANISM: Hevea brasiliensis

<400> SEQUENCE: 5
```

```
Met Ala Asp Leu Lys Ser Thr Phe Leu Lys Val Tyr Ser Val Leu Lys
1               5                   10                  15

Gln Glu Leu Leu Glu Asp Pro Ala Phe Glu Trp Thr Pro Asp Ser Arg
            20                  25                  30

Gln Trp Val Glu Arg Met Leu Asp Tyr Asn Val Pro Gly Gly Lys Leu
        35                  40                  45

Asn Arg Gly Leu Ser Val Ile Asp Ser Tyr Lys Leu Leu Lys Glu Gly
    50                  55                  60

Gln Glu Leu Thr Glu Glu Ile Phe Leu Ala Ser Ala Leu Gly Trp
65                  70                  75                  80

Cys Ile Glu Trp Leu Gln Ala Tyr Phe Leu Val Leu Asp Asp Ile Met
                85                  90                  95

Asp Ser Ser His Thr Arg Arg Gly Gln Pro Cys Trp Phe Arg Val Pro
            100                 105                 110

Lys Val Gly Leu Ile Ala Ala Asn Asp Gly Ile Leu Leu Arg Asn His
        115                 120                 125

Ile Pro Arg Ile Leu Lys Lys His Phe Arg Gly Lys Ala Tyr Tyr Val
    130                 135                 140

Asp Leu Leu Asp Leu Phe Asn Glu Val Glu Phe Gln Thr Ala Ser Gly
145                 150                 155                 160

Gln Met Ile Asp Leu Ile Thr Thr Leu Glu Gly Glu Lys Asp Leu Ser
                165                 170                 175

Lys Tyr Thr Leu Ser Leu His Arg Arg Ile Val Gln Tyr Lys Thr Ala
            180                 185                 190

Tyr Tyr Ser Phe Tyr Leu Pro Val Ala Cys Ala Leu Leu Ile Ala Gly
        195                 200                 205

Glu Asn Leu Asp Asn His Ile Val Val Lys Asp Ile Leu Val Gln Met
210                 215                 220

Gly Ile Tyr Phe Gln Val Gln Asp Asp Tyr Leu Asp Cys Phe Gly Asp
225                 230                 235                 240

Pro Glu Thr Ile Gly Lys Ile Gly Thr Asp Ile Glu Asp Phe Lys Cys
                245                 250                 255

Ser Trp Leu Val Val Lys Ala Leu Glu Leu Cys Asn Glu Glu Gln Lys
            260                 265                 270

Lys Val Leu Tyr Glu His Tyr Gly Lys Ala Asp Pro Ala Ser Val Ala
        275                 280                 285

Lys Val Lys Val Leu Tyr Asn Glu Leu Lys Leu Gln Gly Val Phe Thr
    290                 295                 300

Glu Tyr Glu Asn Glu Ser Tyr Lys Lys Leu Val Thr Ser Ile Glu Ala
305                 310                 315                 320

His Pro Ser Lys Pro Val Gln Ala Val Leu Lys Ser Phe Leu Ala Lys
                325                 330                 335

Ile Tyr Lys Arg Gln Lys
            340

<210> SEQ ID NO 6
<211> LENGTH: 371
<212> TYPE: PRT
<213> ORGANISM: Saccharomyces cerevisiae

<400> SEQUENCE: 6

Met Thr Glu Arg Asn His Leu Lys Ile Asp Lys Ser Asp Val Pro Glu
1               5                   10                  15

Asp Pro Ile Tyr Ser Lys Pro Ser Gln Asn Leu Phe Gln Arg Pro
            20                  25                  30
```

Ala Ser Ser Ile Ser Pro Leu His Ile Leu His Gly Ile Lys Pro Leu
        35                  40                  45

Asn Pro Leu Thr Lys Gly Pro Glu Pro Leu Pro Glu Glu Thr Phe Asp
 50                  55                  60

Lys Gln Arg Gly Ile Leu Pro Lys Gln Arg Arg Leu Ala Glu Ile Val
 65                  70                  75                  80

Glu Met Ile His Thr Ala Ser Leu Leu His Asp Asp Val Ile Asp His
                     85                  90                  95

Ser Asp Thr Arg Arg Gly Arg Pro Ser Gly Asn Thr Ala Phe Thr Asn
                100                 105                 110

Lys Met Ala Val Leu Ala Gly Asp Phe Leu Leu Gly Arg Ala Thr Val
                115                 120                 125

Ser Ile Ser Arg Leu His Asn Pro Glu Val Val Glu Leu Met Ser Asn
130                 135                 140

Ser Ile Ala Asn Leu Val Glu Gly Glu Phe Met Gln Leu Lys Asn Thr
145                 150                 155                 160

Ser Ile Asp Ala Asp Ile Asp Thr Ile Glu Asn Gly His Lys Leu Leu
                165                 170                 175

Pro Val Pro Ser Lys Lys Leu Glu Val Lys Glu His Asp Phe Arg Val
                180                 185                 190

Pro Ser Arg Gln Gln Gly Leu Gln Leu Ser His Asp Gln Ile Ile Glu
                195                 200                 205

Thr Ala Phe Glu Tyr Tyr Ile His Lys Thr Tyr Leu Lys Thr Ala Ala
                210                 215                 220

Leu Ile Ser Lys Ser Cys Arg Cys Ala Ala Ile Leu Ser Gly Ala Ser
225                 230                 235                 240

Pro Ala Val Ile Asp Glu Cys Tyr Asp Phe Gly Arg Asn Leu Gly Ile
                245                 250                 255

Cys Phe Gln Leu Val Asp Asp Met Leu Asp Phe Thr Val Ser Gly Lys
                260                 265                 270

Asp Leu Gly Lys Pro Ser Gly Ala Asp Leu Lys Leu Gly Ile Ala Thr
                275                 280                 285

Ala Pro Val Leu Phe Ala Trp Lys Glu Asp Pro Ser Leu Gly Pro Leu
                290                 295                 300

Ile Ser Arg Asn Phe Ser Glu Arg Gly Asp Val Glu Lys Thr Ile Asp
305                 310                 315                 320

Ser Val Arg Leu His Asn Gly Ile Ala Lys Thr Lys Ile Leu Ala Glu
                325                 330                 335

Glu Tyr Arg Asp Lys Ala Leu Gln Asn Leu Arg Asp Ser Leu Pro Glu
                340                 345                 350

Ser Asp Ala Arg Ser Ala Leu Glu Phe Leu Thr Asn Ser Ile Leu Thr
                355                 360                 365

Arg Arg Lys
    370

<210> SEQ ID NO 7
<211> LENGTH: 406
<212> TYPE: PRT
<213> ORGANISM: Arabidopsis thaliana

<400> SEQUENCE: 7

Met Met Thr Ser Cys Arg Asn Ile Asp Leu Gly Thr Met Met Met Ala
1               5                   10                  15

Cys Gly Cys Gly Arg Arg Gln Phe Pro Ser Leu Ala Lys Thr Val Cys

```
                20                  25                  30
Lys Phe Thr Ser Ser Asn Arg Ser Tyr Gly Gly Leu Val Gly Ser Cys
            35                  40                  45
Lys Ala Val Pro Thr Lys Ser Lys Glu Ile Ser Leu Leu Asn Gly Ile
        50                  55                  60
Gly Gln Ser Gln Thr Val Ser Phe Asp Leu Lys Gln Glu Ser Lys Gln
65                  70                  75                  80
Pro Ile Ser Leu Val Thr Leu Phe Glu Leu Val Ala Val Asp Leu Gln
                85                  90                  95
Thr Leu Asn Asp Asn Leu Leu Ser Ile Val Gly Ala Glu Asn Pro Val
            100                 105                 110
Leu Ile Ser Ala Ala Glu Gln Ile Phe Gly Ala Gly Gly Lys Arg Met
        115                 120                 125
Arg Pro Gly Leu Val Phe Leu Val Ser His Ala Thr Ala Glu Leu Ala
    130                 135                 140
Gly Leu Lys Glu Leu Thr Thr Glu His Arg Arg Leu Ala Glu Ile Ile
145                 150                 155                 160
Glu Met Ile His Thr Ala Ser Leu Ile His Asp Asp Val Leu Asp Glu
                165                 170                 175
Ser Asp Met Arg Arg Gly Lys Glu Thr Val His Glu Leu Phe Gly Thr
            180                 185                 190
Arg Val Ala Val Leu Ala Gly Asp Phe Met Phe Ala Gln Ala Ser Trp
        195                 200                 205
Tyr Leu Ala Asn Leu Glu Asn Leu Glu Val Ile Lys Leu Ile Ser Gln
    210                 215                 220
Val Ile Lys Asp Phe Ala Ser Gly Glu Ile Lys Gln Ala Ser Ser Leu
225                 230                 235                 240
Phe Asp Cys Asp Thr Lys Leu Asp Glu Tyr Leu Leu Lys Ser Phe Tyr
                245                 250                 255
Lys Thr Ala Ser Leu Val Ala Ala Ser Thr Lys Gly Ala Ala Ile Phe
            260                 265                 270
Ser Arg Val Glu Pro Asp Val Thr Glu Gln Met Tyr Glu Phe Gly Lys
        275                 280                 285
Asn Leu Gly Leu Ser Phe Gln Ile Val Asp Asp Ile Leu Asp Phe Thr
    290                 295                 300
Gln Ser Thr Glu Gln Leu Gly Lys Pro Ala Gly Ser Asp Leu Ala Lys
305                 310                 315                 320
Gly Asn Leu Thr Ala Pro Val Ile Phe Ala Leu Glu Arg Glu Pro Arg
                325                 330                 335
Leu Arg Glu Ile Ile Glu Ser Glu Phe Cys Glu Ala Gly Ser Leu Glu
            340                 345                 350
Glu Ala Ile Glu Ala Val Thr Lys Gly Gly Ile Lys Arg Ala Gln
        355                 360                 365
Glu Leu Ala Arg Glu Lys Ala Asp Asp Ala Ile Lys Asn Leu Gln Cys
    370                 375                 380
Leu Pro Arg Ser Gly Phe Arg Ser Ala Leu Glu Asp Met Val Leu Tyr
385                 390                 395                 400
Asn Leu Glu Arg Ile Asp
                405

<210> SEQ ID NO 8
<211> LENGTH: 376
<212> TYPE: PRT
<213> ORGANISM: Homo sapiens
```

<400> SEQUENCE: 8

```
Met Pro Ala Gln Ala His Arg Gln Lys Gly Leu Asp Leu Ser Gln Ile
1               5                   10                  15

Pro Tyr Phe Asn Leu Val Lys His Leu Thr Pro Ala Cys Pro Asn Val
            20                  25                  30

Tyr Ser Ile Ser Gln Phe His His Thr Thr Pro Tyr Ser Lys Thr His
        35                  40                  45

Ser Gly Glu Lys Tyr Thr Asp Pro Phe Lys Leu Gly Trp Arg Asp Leu
    50                  55                  60

Lys Gly Leu Tyr Glu Gly Ile Arg Lys Glu Pro Leu Ile Ser Thr Thr
65                  70                  75                  80

Glu Leu Lys Glu Ile Ser Glu Tyr Tyr Phe Asp Val Lys Gly Lys Ala
                85                  90                  95

Phe Arg Pro Ile Ile Val Val Leu Met Ala Arg Ala Cys Asn Ile His
            100                 105                 110

His Asn Asn Ser Arg His Val Gln Ala Ser Gln Arg Ala Ile Ala Leu
        115                 120                 125

Ile Ala Glu Met Ile His Thr Ala Ser Leu Val His Asp Asp Val Ile
130                 135                 140

Asp Asp Ala Ser Ser Arg Arg Gly Lys His Thr Val Asn Lys Ile Trp
145                 150                 155                 160

Gly Glu Lys Lys Ala Val Leu Ala Gly Asp Leu Ile Leu Ser Ala Ala
                165                 170                 175

Ser Ile Ala Leu Ala Arg Ile Gly Asn Thr Thr Val Ile Ser Ile Leu
            180                 185                 190

Thr Gln Val Ile Glu Asp Leu Val Arg Gly Glu Phe Leu Gln Leu Gly
        195                 200                 205

Ser Lys Glu Asn Glu Asn Glu Arg Phe Ala His Tyr Leu Glu Lys Thr
210                 215                 220

Phe Lys Lys Thr Ala Ser Leu Ile Ala Asn Ser Cys Lys Ala Val Ser
225                 230                 235                 240

Val Leu Gly Cys Pro Asp Pro Val Val His Glu Ile Ala Tyr Gln Tyr
                245                 250                 255

Gly Lys Asn Val Gly Ile Ala Phe Gln Leu Ile Asp Asp Val Leu Asp
            260                 265                 270

Phe Thr Ser Cys Ser Asp Gln Met Gly Lys Pro Thr Ser Ala Asp Leu
        275                 280                 285

Lys Leu Gly Leu Ala Thr Gly Pro Val Leu Phe Ala Cys Gln Gln Phe
290                 295                 300

Pro Glu Met Asn Ala Met Ile Met Arg Arg Phe Ser Leu Pro Gly Asp
305                 310                 315                 320

Val Asp Arg Ala Arg Gln Tyr Val Leu Gln Ser Asp Gly Val Gln Gln
                325                 330                 335

Thr Thr Tyr Leu Ala Gln Gln Tyr Cys His Glu Ala Ile Arg Glu Ile
            340                 345                 350

Ser Lys Leu Arg Pro Ser Pro Glu Arg Asp Ala Leu Ile Gln Leu Ser
        355                 360                 365

Glu Ile Val Leu Thr Arg Asp Lys
370                 375
```

<210> SEQ ID NO 9
<211> LENGTH: 336
<212> TYPE: PRT

<213> ORGANISM: Mus musculus

<400> SEQUENCE: 9

```
Met Cys Ser Cys Arg Gln Thr Gln Ser Gly Glu Lys Tyr Ser Asp Pro
1               5                   10                  15
Phe Lys Leu Gly Trp Arg Asp Leu Lys Gly Leu Tyr Glu Asp Ile Arg
            20                  25                  30
Lys Glu Leu His Ile Ser Thr Arg Glu Leu Lys Asp Met Ser Glu Tyr
        35                  40                  45
Tyr Phe Asp Gly Lys Gly Lys Ala Phe Arg Pro Ile Ile Val Val Leu
    50                  55                  60
Met Ala Arg Ala Cys Asn Ile His His Asn Ala Arg Glu Met Gln
65                  70                  75                  80
Ala Ser Gln Arg Ser Ile Ala Leu Val Ala Glu Met Ile His Thr Ala
                85                  90                  95
Thr Leu Val His Asp Asp Val Ile Asp Asp Ala Ser Ser Arg Arg Gly
            100                 105                 110
Lys His Thr Val Asn Lys Ile Trp Gly Glu Lys Lys Ala Val Leu Ala
        115                 120                 125
Gly Asp Leu Ile Leu Ser Ala Ala Ser Val Ala Leu Ala Arg Ile Gly
    130                 135                 140
Asn Thr Ala Val Val Ser Met Leu Ala Gln Val Ile Glu Asp Leu Val
145                 150                 155                 160
Arg Gly Glu Phe Leu Gln Leu Gly Ser Lys Glu Asn Glu Asn Glu Arg
                165                 170                 175
Phe Ala His Tyr Leu Glu Lys Thr Phe Lys Thr Ala Ser Leu Ile
            180                 185                 190
Ala Asn Ser Cys Lys Ala Val Ser Val Leu Gly Cys Pro Asp Pro Val
        195                 200                 205
Val His Glu Ile Ala Tyr Gln Tyr Gly Lys Asn Val Gly Ile Ala Phe
    210                 215                 220
Gln Leu Ile Asp Asp Val Leu Asp Phe Thr Ser Cys Ser Asp Gln Met
225                 230                 235                 240
Gly Lys Pro Thr Ser Ala Asp Leu Lys Leu Gly Ile Ala Thr Gly Pro
                245                 250                 255
Val Leu Phe Ala Cys Gln Gln Phe Pro Glu Met Asn Ala Met Ile Met
            260                 265                 270
Arg Arg Phe Ser Leu Pro Gly Asp Val Asp Arg Ala Arg Gln Tyr Val
        275                 280                 285
Leu Gln Ser Asp Gly Val Gln Gln Thr Thr Tyr Leu Ala Gln Gln Tyr
    290                 295                 300
Cys His Lys Ala Val Arg Glu Ile Arg Lys Leu Arg Pro Ser Thr Glu
305                 310                 315                 320
Arg Asp Ala Leu Ile Gln Leu Ser Glu Ser Val Leu Thr Arg Asp Lys
                325                 330                 335
```

<210> SEQ ID NO 10
<211> LENGTH: 1650
<212> TYPE: DNA
<213> ORGANISM: Hevea brasiliensis

<400> SEQUENCE: 10

```
gtagtcacag cataagttgg agcaaacaca aaactacagg cctcccaggt tttaaaaaaa    60
aaaaaaaact tttctacgca taatttttcc aagaaaaata ttttgagga ataatttatt   120
```

```
tttattgttc tgttaaaatc tgaaaataaa gaaaaattac ttcctaatgg ttcaaggaaa     180
aaataataat ttattttttg tttataatat tatgaaaata tttaaattat aaaactttaa     240
tttttatttt tttattgtga aatgtataaa aaatacataa aataataaaa ttgtgtttta     300
gccatcctgg ctgttgaggc cgcaaggccc gcaagcagta gccggtaaag gaaaaaccag     360
gggcaatatt tttgcagggt ttttttttt  tttttctttt aaaagtaaag aacgtatgta     420
tgagtcttaa agatagtaat tttaatagag tctttgatct tatataattc tcacacattt     480
ttacaatctg atgtggaatc ctaaagtact aactcgtgtc tatgcccatc actcgcaaac     540
ttcaatcagg atcacatcat ggactctcat ttttctttg  ttttcactta agtgattaat     600
tttcttttg  tcaaaggtaa agaatataca cacatattag aaacaggatt agataattat     660
aaaaaaagga taattttaat gaattttta  attctatata attcattcac acgtactttc     720
accgcttaat atgtgatatg aaggaattta gccctaattt ggttaagaat taatataaat     780
taaaattata ttgtattaga ttaaattaaa ataaaaatat taaattaatt tttttagaaa     840
aattaaaatt gatcttgaac caaactcaaa taaagttaat ttgatccctt cattttttt    900
ttattttaat gaaatttaa  attgagatct tgtaattttg gaagccattt aaatattatc     960
gatttgctaa taattatgct gaatgtaatt taatggtaaa gaaaataaat aataaaaag    1020
atacatttaa tttaatttaa tttatatatt ttttatttc  aaaaaatttt aaaaaggaac    1080
agattgttaa atctttatt  ttttaattaa attaaattta attgagtctc aaatataata    1140
ttttataatc ttaaaaataa ttttaatatt actgatttaa atttatagat ttaatttaaa    1200
aattttttaaa agtaaagaaa ataattaaga ttttaatttt taagtcgcac gtgatttga    1260
atttaatttt ttaaaaacaa agactaactt attttttat aatttattaa gaaaatcatg    1320
aaaatcccca ttctaaatcg acttctggaa ctgggatgat gcgtttgctt tgcgatactc    1380
catgtgcttt acttacccca taaggatcat gcgcgaatca cgatagaacc aatacaacag    1440
caacacgttt acacgctcct tttcttaaca gctggcctgc cattcccacg aatttccatc    1500
tataagtaga gaggtttggt tttagcatca accataatc ggttgatagc ctccatcagc    1560
gttttcagaa aggcgggttt cttttttgaa acttaagcga ctgcgttttg aattttgatc    1620
ttccattttt gcaaaggaa  atcttcgatt                                     1650

<210> SEQ ID NO 11
<211> LENGTH: 919
<212> TYPE: DNA
<213> ORGANISM: Hevea brasiliensis

<400> SEQUENCE: 11
aaccgtccac caatctttga gttccagtga gtcatctact ggttgcttga cagatccatc      60
aataaaacca tatttctttt tggcccgtaa tgcagtcagc atagctcgcg cccattcttc     120
gtaattctcg cccttcaact gaacttgggt aatcaagtta tctgggttgt cattcgaatt     180
cagtgtttaa gaactaaaag ttttcttccc tgatccagaa ctctcatttt tcttttcatc     240
aaccatggct ctgataccat gtaaaaaaac taagaaattt tggaataaga attcttatct     300
ttattgcccc agaaataaaa tatatatata aaaaaattac agctaacaaa taggtcccta     360
atcaagctaa actaccaaaa ttgtatcaaa gtcatacaac aaaaggtaaa aacagatatg     420
cacacaaaaa ttcctaaaca aatgccctaa ataaatacaa ataagtgac  agctaacagc     480
tgcatttcca ataattaatt taactaataa aatttataat cttaaaaata attttaatat     540
tattgaatta aaatttataa ataaaattaa cactgttaaa attaaaagaa aattattaag     600
```

```
atttgaattt ttaagcggtt atttaatttt gaaaaacaag gctaactttt tttttttatat    660 aatttactaa aaaattcatg aatgaaaaaa aaaaatccat aagtaaactt accccatacg    720
ggttatgcac gctaaaccaa taaaacagaa acacgtttat acactcgttt tcatttccat    780
ctataaatag agagatttgt ttttagtttt aaaccataat cagttgatag cttccacagt    840
gttttccgaa aggcaaatct tttttcaaac ttcagcgact gcgttttgaa tttgtgattt    900
ttaaaggaaa ttttcaatt                                                919

<210> SEQ ID NO 12
<211> LENGTH: 1680
<212> TYPE: DNA
<213> ORGANISM: Hevea brasiliensis

<400> SEQUENCE: 12
ggctacctta ttgggaacta ccaatttgtg gattgtggtg attgaattaa ctaataagca     60
actgaatgtt aatttccaga ataagaaaac ttgctgattg taatctcaag ttctagagtg    120
aaaataaaga taattatata aaatatatgg aaattattat cctagaggaa attttatttt    180
tttttaaatt aataaaattt ttgtaattaa aaattttacg aaaaaaaatc taataaaata    240
aatttatgta aaattacttt atttttttata ataaaataat tacattatgt atgaaactaa    300
gtaatcatag aatatatata tatattattt agtttatgtg tcaaatataa tagattaata    360
ttttctttat tattttttcaa aataattttc atgtcaaccc aattaaataa atatccaact    420 aattttttttt ttaaatattt ttatttcaca gagaataatt tgtatataaa aaataatttt    480
cataaaaata tttttttatta tttaattttta acattaatta atggtacgtg ttcatattat    540
atatgaataa tattttttata ttttaataaa attatcaaag ttgagaaaat gatttgctct    600
tttaagttct ctcttaaaaa agaaagtcat ttttcttaaa aataatttaa tttctctttg    660
actaaaatat ttttttgttaa ttatttttttt aatactccaa acacaaaaaa tgtgaaaaaa    720
aaaatatttt ccacgacaca aacaaacaga attttagcca atcaattagc gcaattttca    780
actcccccgc ctcctaaagg ctggactggt gttgttcctg gaggctgata tcctaagcag    840
gtttctggat ttgcactgat tccatgatgg ttgaggcaag agggtatttc taatgagttt    900
ttatttagcc ctcttggttg ttgcctgcca ctggaaatca ccatggaaac atatatgaag    960
tcaaatgaca attttatttt ttttaaatttttt ctgagagtga ggaaatgaat aagaagaatt   1020
tgttattttt ctttaaagtc gtgttacttt tacataatat attaagtcaa atttatcgac   1080
tcagtgaaaa taatttatat tttataaata agaaaaatct tgttatataa tttaatataa   1140
attttatatc tttttttttt caaggaaata aattttatat cttgatgata agatagagat   1200
aagatcgagt taacccttgc gttaattgga tgtttaaatg cttaatgcat ggctaaggaa   1260
attaatgtct aaaataacag aaatgagaaa aataaatgaa gggtgaaaaa taaataaaac   1320
ctggccctat gctctatatt ggggatggag tgggagccac ctaatgtgtc agtgttcatc   1380
ttcgaacaac gactcgattc aaagcacacc catgaagccg cttcacatca tccctttgaa   1440
actttccacc ctaatcagct atcacacgat ctactttcca atctcatcaa cgctccaaat   1500
ctcaccacca ttcagtccac tttcacttcc tccttgtcct aatcatcttt aatccatcgg   1560
ggtattatgg taattacatg atcaagtctc tctgctataa ataaagccaa gtgagcttag   1620
ctcatcatca catcatttgc ataccagaaa atcaagaatt gggaagaaat gggaagagtt   1680

<210> SEQ ID NO 13
```

```
<211> LENGTH: 1610
<212> TYPE: DNA
<213> ORGANISM: Hevea brasiliensis

<400> SEQUENCE: 13
taccagctat gattcacctc tagtgatatt gattttatta aaaattaagg caatgatgaa       60 tttcttttttg aaaaaatcat ttaagattca agagggagat acagtgatgt cgttattttt      120
taattttatg taagtaaaat tcgtcaatca ttcatcaaag ttaactgcgt gctaaataat      180
ttaaaaatta ttgtttttta ttttttgaaaa ttataataaa attcatttgt tttaataatt      240
aggttcttag tttataattt ttttatttta aatttaagta tttatgatta attctgattt      300
aatttctgat aattttaaaa ttaaaattat ttgattctta caaattttta acaatcattg      360
ttttagacca atctcaaagt aaatgtttca cacgttacaa gggtgcaaaa tgattggacg      420
gtgacagaaa cagtaaatat tatgaattta attgttgcca tgggctgcta aattcaaagg      480
gtcatcatta cgtgattctc gatttacgaa aaaaaaaaag tattttcata tatatatgta      540
tatacacaca cacatcatgc aaaatattta gttaataatt ttccaaaatt aaaactttt      600 tttatagcat acaattaaaa tgttaaattc aattaaaaaa gtgaaaataa aatataatt      660 ttttacataa aaaatataaa ttttatataa ttattagtga gaatatatat tactagattt      720
aaaatatact gaataaccac tcgcttttta attggttata gtgattaatt aagaattttt      780
tttatctaaa tttattaagt gatccaacaa attttgaact attatataag tttataaaat      840
tttgattctc cattctacat ttttaaattt tcatttttta tattatgaaa atatatacat      900
aaaaaaatta attaaactag agttaattgt cagaatgaat ctctagtaaa attttctctg      960
attaaaaaat aaatttcata aattatccca ctaaactttt gtcatgtgat catgtcccca     1020
ataaaatttg atttattat aattggcaac tcgatgtcta acctgcgagt aattatacac     1080
catccccatg atacctccat gatttcaagt gtcaaagtat gttttaatga gaaattatta     1140
ggttaactca atgtatatac attattttttt ataattatgt gaaattaatt ctcataatta     1200
tataggacac atacttcgtc cacttatttt ttagaaaaaa agcattattt tttagcactt     1260
tcaatgtaac taataattaa cggttttttaa catgtaagta taattgaata ttataaaacg     1320
cattaataca tatatatgca tgattcttgt taatttacca ttctacgtag aatattccat     1380
atagaatcaa tgctttatta tataataatt tctgctacat aataagaggc tttcatttcc     1440
tttgtcttta aataaccccca agtctcactt gtaaaccaac gtcgctcatt tatccctctt     1500
accctgtccc tctccaactc tcaaactttt tggaattcca tagattgtgg aaactctcta     1560
gctaaaccaa aaaacagaaa agaacataca aaattgaaat actaaggtgc               1610

<210> SEQ ID NO 14
<211> LENGTH: 39
<212> TYPE: DNA
<213> ORGANISM: Artificial Sequence
<220> FEATURE:
<223> OTHER INFORMATION: PRIMER-1

<400> SEQUENCE: 14
ctgtattttc agggcggata tgtttcttcg accaaggcc                              39

<210> SEQ ID NO 15
<211> LENGTH: 41
<212> TYPE: DNA
<213> ORGANISM: Artificial Sequence
<220> FEATURE:
<223> OTHER INFORMATION: PRIMER-2
```

<400> SEQUENCE: 15
caaaactagt gcggccgcgc taatcaatcc gttcgagatt g          41

<210> SEQ ID NO 16
<211> LENGTH: 34
<212> TYPE: DNA
<213> ORGANISM: Artificial Sequence
<220> FEATURE:
<223> OTHER INFORMATION: PRIMER-3

<400> SEQUENCE: 16
tttggatccg atggaattat acaacggtga gagg          34

<210> SEQ ID NO 17
<211> LENGTH: 39
<212> TYPE: DNA
<213> ORGANISM: Artificial Sequence
<220> FEATURE:
<223> OTHER INFORMATION: PRIMER-4

<400> SEQUENCE: 17
tttgcggccg cttatttaa gtattcctta tgtttctcc          39

<210> SEQ ID NO 18
<211> LENGTH: 873
<212> TYPE: DNA
<213> ORGANISM: Hevea brasiliensis

<400> SEQUENCE: 18
atggaattat acaacggtga gaggccaagt gtgttcagac ttttagggaa gtatatgaga          60
aaagggttat atagcatcct aacccagggt cccatcccta tcatattgc cttcatattg         120
gatggaaaca ggaggtttgc taagaagcat aaactgccag aaggaggtgg tcataaggct         180
ggattttag ctcttctgaa cgtactaact tattgctatg agttaggagt gaaatatgcg         240
actatctatg cctttagcat cgataatttt cgaaggaaac tcatgaggt tcagtacgta         300
atggatctaa tgctggagaa gattgaaggg atgatcatgg aagaaagtat catcaatgca         360
tatgatattt gcgtacgttt tgtgggtaac ctgaagcttt taagtgagcc agtcaagacc         420
gcagcagata agattatgag ggctactgcc aacaattcca atgtgtgct tctcattgct         480
gtatgctata cttcaactga tgagatcgtg catgctgttg aagaatcctc tgaattgaac         540
tccaatgaag tttgtaacaa tcaagaattg gaggaggcaa atgcaactgg aagcggtact         600
gtgattcaaa ttgagaacat ggagtcgtat tctggaataa aacttgtaga ccttgagaaa         660
aacacctaca taaatcctta tcctgatgtt ctgattcgaa cttctgggga gacccgtctg         720
agcaactact tactttggca gactactaat tgcatactgt attctcctca tgcactgtgg         780
ccagagattg gtcttcgaca cgtggtgtgg gcagtaatta acttccaacg tcattattct         840
tacttggaga aacataagga atacttaaaa taa                                      873

<210> SEQ ID NO 19
<211> LENGTH: 290
<212> TYPE: PRT
<213> ORGANISM: Hevea brasiliensis

<400> SEQUENCE: 19

Met Glu Leu Tyr Asn Gly Glu Arg Pro Ser Val Phe Arg Leu Leu Gly
1               5                   10                  15

Lys Tyr Met Arg Lys Gly Leu Tyr Ser Ile Leu Thr Gln Gly Pro Ile

-continued

```
                     20                  25                  30
Pro Thr His Ile Ala Phe Ile Leu Asp Gly Asn Arg Arg Phe Ala Lys
            35                  40                  45

Lys His Lys Leu Pro Glu Gly Gly His Lys Ala Gly Phe Leu Ala
    50                  55                  60

Leu Leu Asn Val Leu Thr Tyr Cys Tyr Glu Leu Gly Val Lys Tyr Ala
65                      70                  75                  80

Thr Ile Tyr Ala Phe Ser Ile Asp Asn Phe Arg Arg Lys Pro His Glu
                85                  90                  95

Val Gln Tyr Val Met Asp Leu Met Leu Glu Lys Ile Glu Gly Met Ile
                100                 105                 110

Met Glu Glu Ser Ile Ile Asn Ala Tyr Asp Ile Cys Val Arg Phe Val
                115                 120                 125

Gly Asn Leu Lys Leu Leu Ser Glu Pro Val Lys Thr Ala Ala Asp Lys
            130                 135                 140

Ile Met Arg Ala Thr Ala Asn Asn Ser Lys Cys Val Leu Leu Ile Ala
145                 150                 155                 160

Val Cys Tyr Thr Ser Thr Asp Glu Ile Val His Ala Val Glu Glu Ser
                165                 170                 175

Ser Glu Leu Asn Ser Asn Glu Val Cys Asn Asn Gln Glu Leu Glu Glu
                180                 185                 190

Ala Asn Ala Thr Gly Ser Gly Thr Val Ile Gln Ile Glu Asn Met Glu
            195                 200                 205

Ser Tyr Ser Gly Ile Lys Leu Val Asp Leu Glu Lys Asn Thr Tyr Ile
    210                 215                 220

Asn Pro Tyr Pro Asp Val Leu Ile Arg Thr Ser Gly Glu Thr Arg Leu
225                 230                 235                 240

Ser Asn Tyr Leu Leu Trp Gln Thr Thr Asn Cys Ile Leu Tyr Ser Pro
                245                 250                 255

His Ala Leu Trp Pro Glu Ile Gly Leu Arg His Val Val Trp Ala Val
            260                 265                 270

Ile Asn Cys Gln Arg His Tyr Ser Tyr Leu Glu Lys His Lys Glu Tyr
            275                 280                 285

Leu Lys
    290
```